United States Patent
Blatter

(12) 
(10) Patent No.: US 6,656,151 B1
(45) Date of Patent: *Dec. 2, 2003

(54) VASCULAR ACCESS DEVICES AND SYSTEMS

(75) Inventor: Duane D. Blatter, Salt Lake City, UT (US)

(73) Assignee: Integrated Vascular Interventional Technologies, L.C. (IVIT, LC), Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/480,964

(22) Filed: Jan. 11, 2000

(51) Int. Cl.$^7$ .............................................. A61M 29/00
(52) U.S. Cl. ................. 604/96.01; 604/891.1; 604/288.01
(58) Field of Search ................. 606/153, 158, 606/151, 213, 219, 184; 604/891.1, 103.01, 103.02, 96.01, 264, 288.01

(56) References Cited

U.S. PATENT DOCUMENTS

| | | | |
|---|---|---|---|
| 3,392,722 A | 7/1968 | Jorgensen | 128/1 |
| 3,395,710 A | 8/1968 | Stratton et al. | 128/350 |

(List continued on next page.)

FOREIGN PATENT DOCUMENTS

| | | | |
|---|---|---|---|
| WO | WO 98/19629 | 5/1998 | A61F/2/06 |
| WO | WO 98/19634 | 5/1998 | A61F/2/06 |

OTHER PUBLICATIONS

Apparatus, Hemoperfusion, Sorbent on Neoforma, *the global healthcare marketplace, Gastroenterology/Urology,* located at http://www.neoforma-gu.com/n0o/cat-gu/n0orj67ul.html, 1 pg., printed Dec. 17, 1999.

Xact Medicare Services, Xact Medicare Policy S–107: Hemoperfusion, *Medicare Medical Policy Bulletin, Freedom of Information,* located at http://www.xact.org/policy/s107.html, 1 pg., printed Dec. 17, 1999.

Xact Medicare Services, Xact Medicare Policy S–53: Hemofiltration (Diafiltration) *Medicare Medical Policy Bulletin, Freedom of Information,* located at http://www.xact.org/policy/s107.html, 1 pg., printed Dec. 17, 1999.

Facts about Plasmapheresis, *Plasmapheresis and Autoimmune Disease,* MDA Publications, located at http://www.mdausa.org/publications/fa–plasmaph.html, 4 pgs., printed Dec. 9, 1999.

Publications, *Hemodialysis,* located at http://www.rein.ca/hem-e.htm, 4 pgs., printed Dec. 9, 1999.

*Good Nutrition & Hemodialysis,* located at http://www.nyu.edu/classes/compnutrfood/Cecilia%20Fong/index.html 1 pg., printed Dec. 9, 1999.

(List continued on next page.)

*Primary Examiner*—Brian L. Casler
*Assistant Examiner*—Kevin C. Sirmons
(74) *Attorney, Agent, or Firm*—Stoel Rives LLP

(57) ABSTRACT

Vascular access systems and devices for facilitating repeated access to a blood vessel. These systems and devices can be used in external treatment of blood, such as dialysis, and in intra-venous administration of medicines, such as heparin, for extended periods of time, while avoiding deleterious effects such as those derived from repeated puncturing of the blood vessel tissues or exposure of such tissues to abnormal fluid flows. The vascular access systems comprise an anastomosis graft vessel, an occlusal balloon, and a port device for accessing the occlusal balloon. Occlusal balloons can be self-contained, they can rely on osmosis, and they can serve as the support of an agent to which the blood stream is exposed, either by transport or by mere contact. In addition, occlusal balloons can adopt a distended and a collapsed configuration, the latter allowing for blood flow through the anastomosis graft vessel.

63 Claims, 7 Drawing Sheets

U.S. PATENT DOCUMENTS

| | | | | |
|---|---|---|---|---|
| 3,826,257 | A | 7/1974 | Buselmeier | |
| 3,991,756 | A | 11/1976 | Synder | |
| 4,122,858 | A | 10/1978 | Schiff | |
| 4,301,797 | A | 11/1981 | Pollack | |
| 4,318,401 | A | 3/1982 | Zimmerman | |
| 4,370,983 | A | 2/1983 | Lichtenstein | |
| 4,623,348 | A | 11/1986 | Feit | |
| 4,655,771 | A | 4/1987 | Wallsten | 623/1.22 |
| 4,819,637 | A | 4/1989 | Dormandy, Jr. et al. | 128/325 |
| 4,846,186 | A | 7/1989 | Box et al. | 128/657 |
| 5,092,841 | A * | 3/1992 | Spears | 604/96 |
| 5,102,402 | A * | 4/1992 | Dror et al. | 604/265 |
| 5,211,683 | A | 5/1993 | Maginot | |
| 5,290,306 | A | 3/1994 | Trotta et al. | 606/194 |
| 5,304,220 | A | 4/1994 | Maginot | |
| 5,411,475 | A | 5/1995 | Atala et al. | 604/54 |
| 5,417,657 | A | 5/1995 | Hauer | |
| 5,443,497 | A | 8/1995 | Venbrux | 623/1.13 |
| 5,456,712 | A | 10/1995 | Maginot | 623/1 |
| 5,458,568 | A | 10/1995 | Racchini et al. | |
| 5,478,320 | A | 12/1995 | Trotta | |
| 5,613,979 | A | 3/1997 | Trotta et al. | 606/194 |
| 5,616,114 | A | 4/1997 | Thornton et al. | 600/3 |
| 5,617,878 | A | 4/1997 | Taheri | 128/898 |
| 5,620,649 | A | 4/1997 | Trotta | 264/515 |
| 5,634,936 | A | 6/1997 | Linden et al. | 606/213 |
| 5,662,580 | A | 9/1997 | Bradshaw et al. | 600/3 |
| 5,662,700 | A | 9/1997 | Lazarus | |
| 5,693,088 | A | 12/1997 | Lazarus | |
| 5,695,504 | A | 12/1997 | Gifford, III et al. | 606/153 |
| 5,702,412 | A | 12/1997 | Popov et al. | 606/1 |
| 5,755,775 | A | 5/1998 | Trerotola et al. | |
| 5,766,158 | A | 6/1998 | Opolski | 604/265 |
| 5,779,731 | A | 7/1998 | Leavitt | |
| 5,792,095 | A | 8/1998 | Kissinger et al. | |
| 5,795,325 | A | 8/1998 | Valley et al. | |
| 5,797,879 | A | 8/1998 | DeCampli | |
| 5,797,934 | A | 8/1998 | Rygaard | |
| 5,817,113 | A * | 10/1998 | Gifford, III et al. | 606/153 |
| 5,830,222 | A | 11/1998 | Makower | 606/1 |
| 5,830,228 | A | 11/1998 | Knapp et al. | 606/195 |
| 5,843,027 | A | 12/1998 | Stone et al. | 604/53 |
| 5,868,770 | A | 2/1999 | Rygaard | |
| 5,893,369 | A | 4/1999 | LeMole | |
| 5,925,060 | A | 7/1999 | Forber | 606/191 |
| 5,954,706 | A | 9/1999 | Sahatjian | |
| 5,961,536 | A | 10/1999 | Mickley et al. | |
| 5,976,178 | A | 11/1999 | Goldsteen et al. | 623/1 |
| 6,007,576 | A | 12/1999 | McClellan | |
| 6,030,392 | A | 2/2000 | Dakov | 606/139 |
| 6,042,569 | A | 3/2000 | Finch, Jr. et al. | |
| 6,068,637 | A | 5/2000 | Popov et al. | 606/159 |
| 6,086,553 | A | 7/2000 | Akbik | |
| 6,102,884 | A | 8/2000 | Squitieri | |
| 6,113,612 | A | 9/2000 | Swanson et al. | |
| 6,171,319 | B1 | 1/2001 | Nobles et al. | |
| 6,200,257 | B1 | 3/2001 | Winkler | |
| 6,248,117 | B1 * | 6/2001 | Blatter | 606/153 |
| 6,254,563 | B1 | 7/2001 | Macoviak et al. | |
| 6,261,257 | B1 | 7/2001 | Uflacker et al. | |
| 6,264,633 | B1 * | 7/2001 | Knorig | 604/102 |
| 6,280,460 | B1 | 8/2001 | Bolduc et al. | 606/222 |
| 6,293,965 | B1 | 9/2001 | Berg et al. | 623/1.13 |
| 6,319,226 | B1 | 11/2001 | Sherry | |
| 6,401,721 | B1 | 6/2002 | Maginot | |

OTHER PUBLICATIONS

Tennessee Kidney Clinics and Affiliates, *What is Hemodialysis?* located at http://www.dialysisclinics.com/news2.htm, 1 pg., printed Dec. 9, 1999.

*Good Nutrition & Hemodialysis*, located at http://www.nyu.edu/classes/computrfood/Cecilia%20Fong/index.html, 1 pg., printed Dec. 9, 1999.

Lycos, Your Personal Internet Guide, APHERESIS, located at http://infoplease.lycos.com/ipd/A0321273.html, 2 pgs, Dec. 17, 1999.

Clark Biocompatible Hermoperfusion System and Block Cutter, *Some Other Products from Clark Research, Clark® Biocompatible Hemoperfusion*, located at http://www-.clarkrd.com/crd_other2.htm, 2 pgs., printed Dec. 17, 1999.

Mulzer, S.R. and Brash, J.L., *Identification of Plasma Proteins Adsorbed to Hemodialyzers During Clinical Use*, Journal of Biomedical Materials Research, vol. 23, 1483–1504 (1989).

Ljungberg, B., et al., *Effective Anticoagulation by a Low Molecular Weight Heparin (Fragmin®) in Hemodialysis with a Highly Permeable Polysulfone Membrane*, Clinical Nephrology, vol. 38, No. 2–1992 (97–100).

Jen Ming Yang, et al., *Preparation of Heparin Containing SBS–g–VP Copolymer Membrane for Biomaterial Usage*, Journal of Membrane Science 138 (1998) 19–27.

Brittinger, Wolf Dieter et al., *Vascular Access for Hemodialysis in Children*, Pediatric Nephrology, 1997, pp. 11:87–95.

* cited by examiner

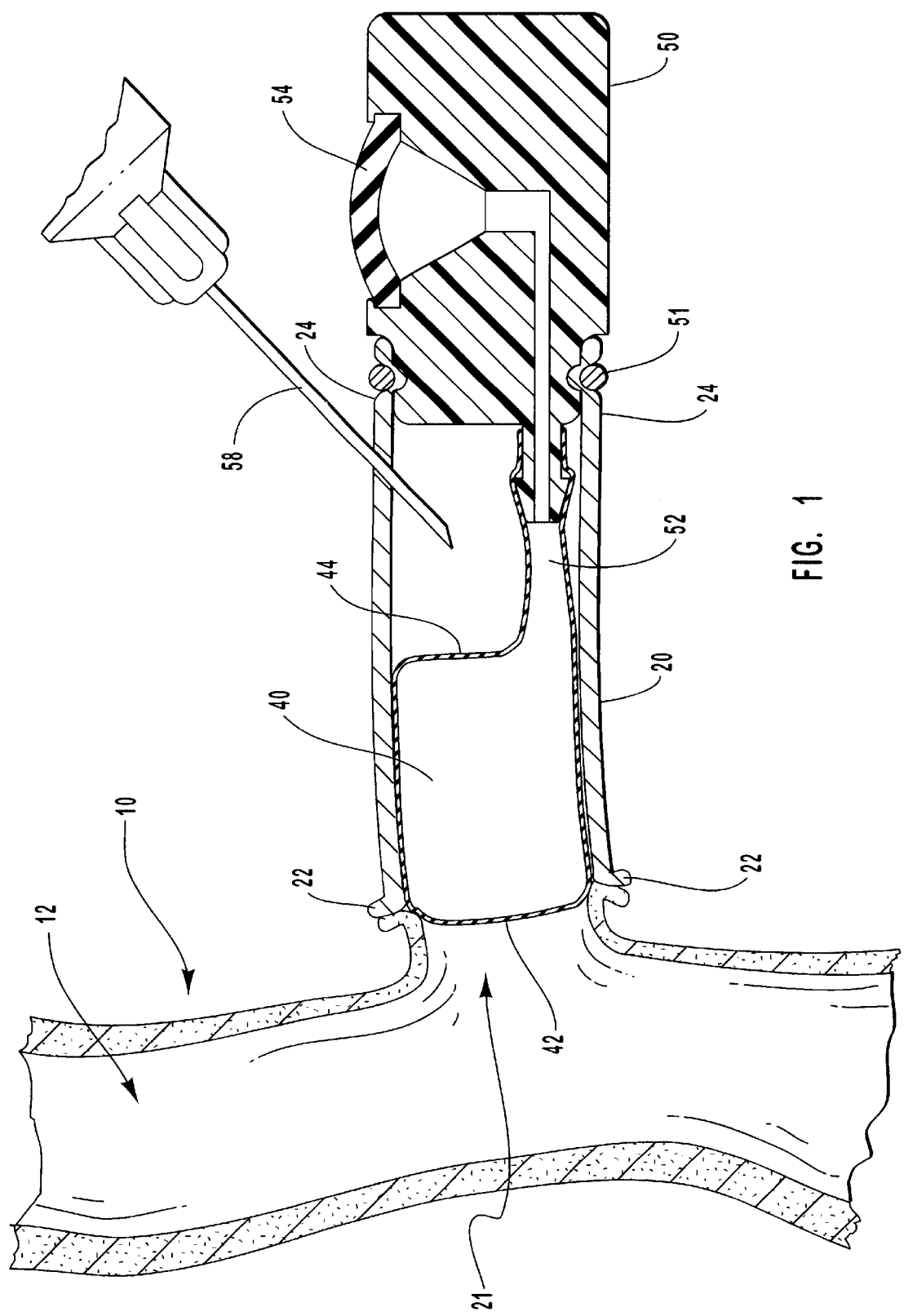

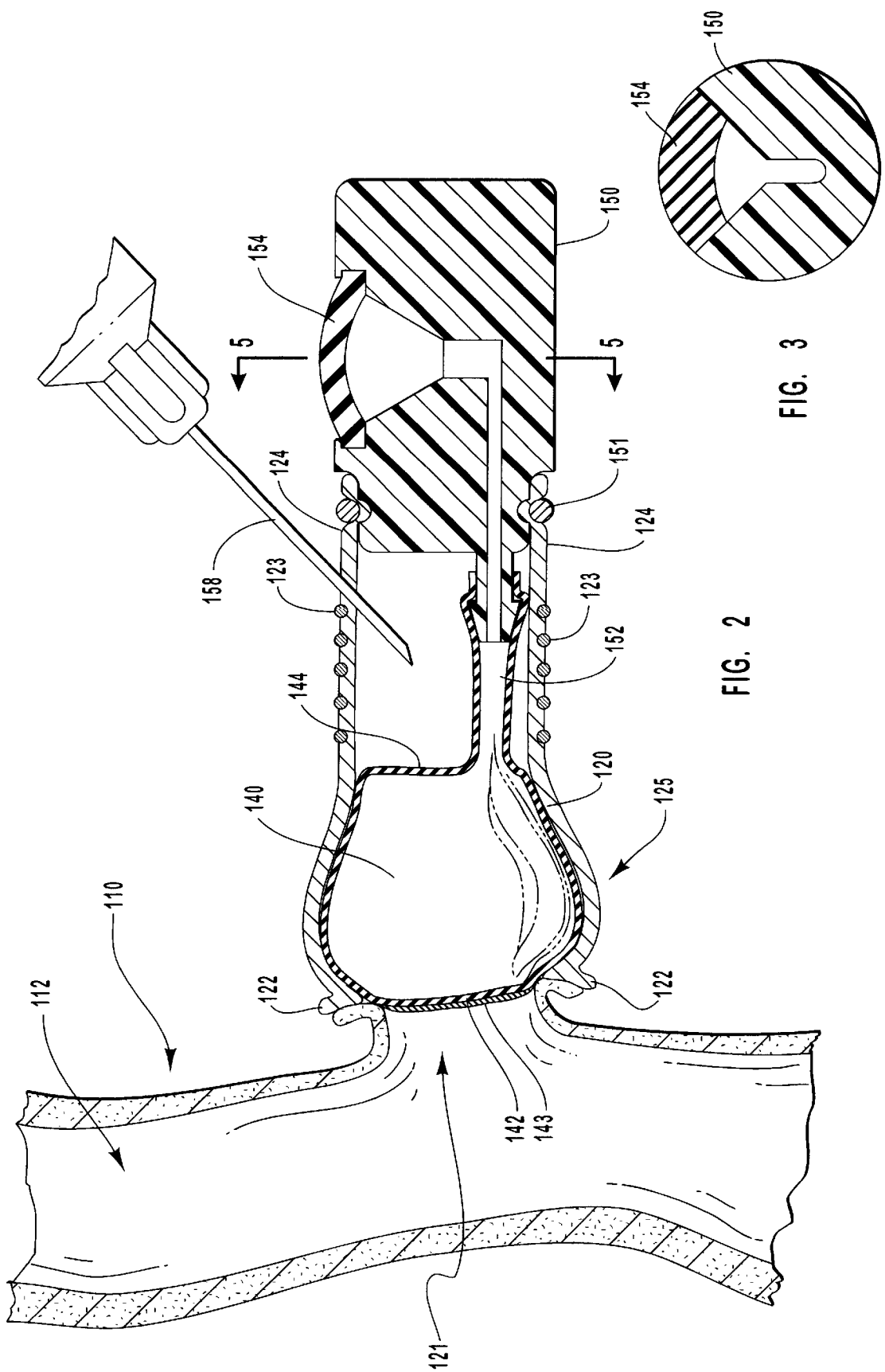

VASCULAR ACCESS DEVICES AND SYSTEMS

BACKGROUND OF THE INVENTION

1. The Field of the Invention

The present invention relates to vascular access systems and devices. In particular, the present invention relates to vascular access systems and devices, that permit access to the blood flow while avoiding repeated punctures into the blood vessel being accessed.

2. Present State of the Art

Procedures that require the repeated access to blood vessels include dialysis and the delivery of medicines for an extended period of time. The multiple punctures that such repeated access necessitates eventually render the blood vessel unsuitable for further effective injections. In addition, some external blood treatment methods rely on the extraction of blood from an artery and on the subsequent injection of the treated blood into a vein. The characteristics of the fluid flow in an artery are significantly different from the characteristics in the fluid flow in a vein. These fluid flow dissimilarities may lead to additional adverse effects that detrimentally affect the long term accessibility of the blood vessels that must be accessed for the external blood treatment to be effectively performed.

It is desirable to provide a device that permits multiple access to a blood vessel for the purpose of delivering medicines into the patient's blood stream in such a way that the receiving blood vessel is not so severely damaged that it becomes unavailable after a few medicine administrations.

It is also desirable to provide a device that permits multiple access to a blood vessel for external blood treatment, such as hemodialysis, in such a way that the blood vessel being accessed does not become unavailable for successive dialysis operations.

Furthermore, it would be desirable to provide a device that is suitable for multiple vascular access for the purpose of long term medicine delivery into the patient's blood flow and also for the purpose of effectively practicing hemodialysis for a long period of time.

The practical advantages of such device would be considerably enhanced if it could be lodged subcutaneously and if it were reliably attachable to a blood vessel by anastomosis techniques. In addition, such vascular access device would have to be appropriately configured to allow for controlled and selected blood flow through it and to allow for a controlled delivery of physiologically active agents, such as medicines. These goals should be accomplished while minimizing, or avoiding to the maximum extent possible, undesirable adverse effects such as vessel thrombosis, blood stagnation, the formation of undesirable turbulence, and the formation of blood clots.

The present invention focuses on objectives described hereinbelow for solving problems which are associated with repeated vascular access, and provides devices with advantageous features for solving such problems.

OBJECTS AND BRIEF SUMMARY OF THE INVENTION

A blood vessel that is repeatedly accessed, and in particular repeatedly punctured, deteriorates to the point that vascular access becomes increasingly difficult and eventually impossible. When vascular access places the blood vessel under exceptional fluid dynamics conditions or subjects the vascular tissues to the deleterious side effects of certain medications, vascular deterioration can be seriously accelerated.

Although an occasional vascular access can be performed at any one among a plurality of generally available access sites, the availability of vascular access sites for the intravenous delivery of medicine for a long period of time or for dialysis can be seriously diminished because vascular access under such conditions has to be performed repeatedly. For example, hemodialysis typically requires from about 150 to about 200 vascular access operations per year for a period that typically ranges form about 2 years to about 5 years.

It is therefore desirable to provide vascular access devices and systems that can be repeatedly accessed, and in particular repeatedly punctured, while avoiding the deleterious effects on the blood vessel itself. These systems and devices should be biocompatible and in particular they should not significantly perturb the normal blood flow within the blood vessel that is to be accessed. In addition, these systems and devices should be made of readily available materials that can be clinically manipulated according to known techniques.

The general object of this invention is to provide vascular access systems and devices that facilitate repeated vascular access while reducing, or even eliminating, the deleterious effects that the vascular tissue would otherwise be subjected to. More specifically, it is an object of this invention to provide vascular access systems and devices that permit access to the blood stream while avoiding repeated punctures into the blood vessel being accessed.

It is another object of this invention to provide vascular access systems and devices that can be attached to a blood vessel by known anastomosis techniques.

It is another object of this invention to provide vascular access systems and devices that can be used for the intravenous long term delivery of medicines and also be used in dialysis.

These and other objects of this invention are preferably achieved by devices that comprise an occlusal balloon in fluid communication with a port device, and by systems that comprise an occlusal balloon in fluid communication with a port device to be used in conjunction with a graft vessel that in turn is configured to be anastomosed to a blood vessel.

The devices and systems of this invention preferably feature materials that are suitable for their subcutaneous disposition. This feature advantageously permits the placement of the vascular access systems and devices at a location that is not directly exposed to external pathogens.

The devices and systems of this invention preferably feature materials that can be repeatedly punctured and that are self-sealing. These features advantageously permit multiple injection to and extraction from the vascular access systems and devices of a variety of fluids such as blood samples, biocompatible solutions, medicines, and blood to be dialyzed or to be received from a dialysis apparatus.

The devices and systems of this invention preferably incorporate features that facilitate the exposure of the blood stream to desired physiologically effective (or bioactive) agents. This exposure is achieved by contact or by transport phenomena. In any case, these features advantageously permit, inter alia, the delivery into the blood stream of medications at desired and controlled dosages. Another advantage derived from these features is that the blood stream can be exposed to an agent that prevents the formation of blood clots.

These and other objects, features, and advantages of the present invention will become more fully apparent from the

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 1 is a partial cross sectional view of an embodiment of a vascular access system with an occlusal balloon.

FIG. 2 is a partial cross sectional view of another embodiment of a vascular access system with a reinforced graft vessel that has an enlarged portion, and an occlusal balloon with a semipermeable membrane.

FIG. 3 is a partial cross sectional view of the port device of the embodiment shown in FIG. 2.

DETAILED DESCRIPTION OF THE PREFERRED EMBODIMENTS

Figure 4:
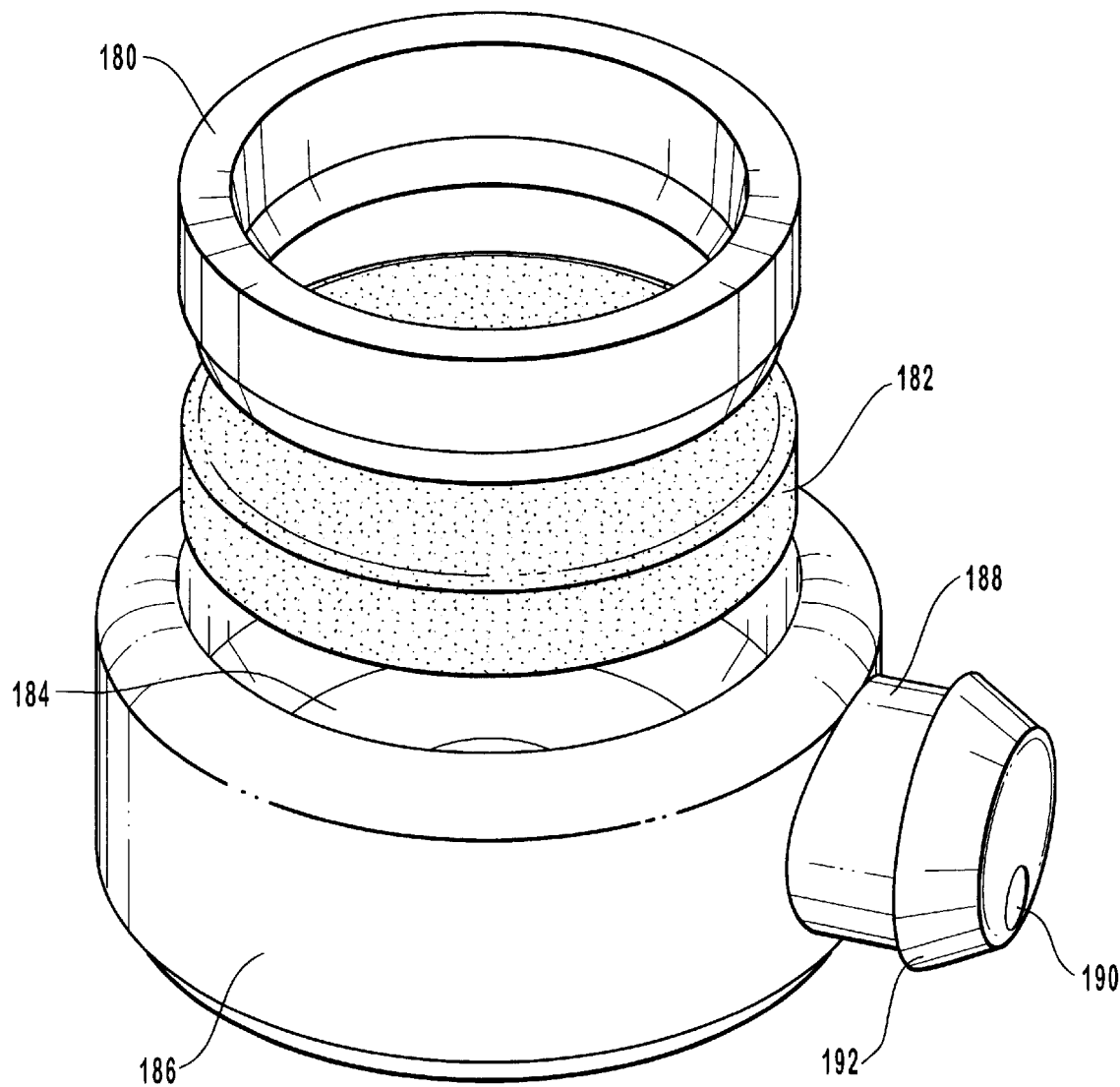
FIG. 4 shows a perspective view of an embodiment of a port device.

The present invention relates to vascular access systems and devices, and in particular to venous access systems and devices, that permit access to the blood flow while avoiding repeated punctures into the blood vessel being accessed. To this end, an exemplary embodiment of the system of the present invention includes the following components: a graft vessel that is adapted for being anastomosed to the blood vessel that is to be repeatedly accessed, an occlusal balloon, a port device, and a semipermeable membrane that permits the selective and controlled exposure of the blood flow to an agent such as a physiologically active agent.

Selective and controlled exposure to a physiologically active agent is, in some preferred embodiments, provided by letting such agent migrate from the interior of an occlusal balloon into the blood in the vessel being accessed. This migration of a physiologically active agent is preferably realized by diffusion across a semipermeable membrane of adequately chosen porosity. In addition, preferred embodiments of the semipermeable membrane function according to the present invention by letting the migration of an aqueous fluid from the blood stream in the vessel being accessed into the interior of an embodiment of an occlusal balloon. This migration of aqueous fluid is preferably realized by permeation across a semipermeable membrane of adequately chosen porosity. By migrating from the blood stream into the interior of an embodiment of an occlusal balloon, this aqueous fluid keeps the occlusal balloon in a distended configuration by osmosis, thus preventing the invasion of the anastomosed graft by blood from the accessed vessel.

FIG. 1 schematically and generally shows in a cross sectional view relevant features of this invention as illustrated by an exemplary embodiment. Blood vessel 10 in this exemplary embodiment is accessed with the aid of graft vessel 20 that is anastomosed to blood vessel 10 at anastomosis site 21. Graft vessel 20 houses, in this particular embodiment, occlusal balloon 40 with a delivery end 42 and an access end 44.

The anastomosed graft of this invention provides a passage for establishing fluid communication with the lumen of the vessel, for example a vein, being accessed. Methods, systems and devices for anastomosing a graft vessel to a blood vessel have been disclosed, for example, in copending US patent application Ser. No. 09/293,336 which is entitled Methods, Systems and Apparatus for Intraluminally Directed Vascular Anastomosis, filed on Apr. 16, 1999, and U.S. Pat. No. 6,248,117 which is entitled Anastomosis Apparatus for Use in Intraluminally Directed Vascular Anastomosis, filed on Apr. 16, 1999. Both applications, including Ser. No. 09/293,336 and U.S. Pat. No. 6,248,117, are herein incorporated by reference in their entirety. The present invention, however, does not require a specific anastomosis technique for its implementation.

A plurality of factors may cause blood flowing in lumen 12 of blood vessel 10 to coagulate in the region near anastomosis site 21 resulting in vessel thrombosis. These factors include the presence of foreign bodies used in the anastomosis procedure, irregularities at anastomosis site 21, and disrupted intima at anastomosis site 21. To prevent this formation of blood clots, blood flowing in lumen 12 is exposed in the region near to delivery end 42 to an anticoagulant agent that is provided with the aid of occlusal balloon 40.

In addition to coagulation, blood flow stagnation in the region near anastomosis site should be minimized and preferably avoided. To this end, occlusal balloon 40 is so configured as to be able to seal the anastomosis site in a way such that no significant cavity is formed at anastomosis site 21; the presence of a cavity or substantially recessed space in this region would lead to blood flow stagnation or to a clot. In addition, a cavity or substantially recessed space can lead to the formation of unacceptably turbulent blood flow when the device is anastomosed to an artery.

Graft vessel 20 is shown in FIG. 1 as being anastomosed to blood vessel 10 which is accessed at anastomosis site 21. Graft vessel 20 has port end 24 which is opposite to anastomosis end 22; port end 24 is in this exemplary embodiment connected to port device 50. Graft vessel 20 and port device 50 are typically located subcutaneously and graft vessel 20 is made of a material such as polytetrafluoroethylene (PTFE) or some other biocompatible self sealing material that can be punctured as schematically shown in FIG. 1 by hypodermic needle 58 or by any other medical device that is ordinarily used to inject fluids in or to draw fluids from a cavity. As illustrated by the embodiment shown in FIG. 1, delivery end 42 of occlusal balloon 40 generally corresponds with anastomosis end 22 of graft vessel 20 in the sense that both ends are generally located in the region of the anastomosis site 21.

The exemplary embodiment of port device 50 shown in FIG. 1 comprises conduit 52 that is connected in fluid communication at one of its ends with occlusal balloon 40 at access end 44. The opposite end of conduit 52 can be externally accessed through a self-sealing aperture 54. This self-sealing aperture can be penetrated by a hypodermic needle or any other medical instrument that is typically used to inject fluid into or to draw fluid from a cavity. Embodiments of the self-sealing aperture according to this invention are preferably made of silicone rubber. Port devices such as port device 50 are common medical devices and hence no further detailed description of the structure of the connection of such a port device to access end 44 is herein sketched. Commercially available port devices for vascular access include devices that are marketed under the trademarks OmegaPort, TitanPort, and Vortex, by Horizon Medical Products, Manchester, Georgia, and under the trademarks P. A. S. Port and P. A. S. Port II by Smiths Industries Medical Systems, or SIMS Deltec, Inc., Saint Paul, Minn.

As shown in the example depicted in FIG. 11 port end 24 of graft vessel 20 is detachably connected to port device 50 by a pressure device 51 that exerts sufficient pressure to maintain the leak proof attachment of graft vessel 20 to port device 50. Pressure device 51 can in particular be embodied by an O-ring or by any other device that exerts sufficient pressure to maintain the leak proof attachment of graft vessel 20 to port device 50. This leak proof attachment can be accomplished in other embodiments of this invention by a threaded engagement, a snap joint engagement, a bound engagement, an adhesive bound engagement, or by any type of leak proof engagement that is well known in the art. Embodiments of the port device are preferably made of stainless steel or titanium, although other biocompatible materials can also be used, particularly other biocompatible materials that are preferably resistant to the abrasion of sharp needle tips.

Occlusal balloon 40 can be inflated with fluid provided thereto through port device 50, in which case occlusal balloon 40 prevents the flow of blood into graft vessel 20 by occluding and effectively sealing anastomosis site 21. Occlusal balloon 40 can be selectively deflated by drawing its fluid content through port device 50, in which case blood flow from blood vessel 10 invades the interior of graft vessel 20 through anastomosis site 21. Embodiments of inflatable balloons according to the present invention, are made of any elastic biocompatible material, such as rubber, PTFE, latex, and combinations of these materials. When the embodiment of the inflatable balloon comprises a membrane that is attached to the balloon with an adhesive, the balloon material is preferably gluable, such as silicone rubber.

When blood flow from blood vessel 10 reaches the interior of graft vessel 20 because occlusal balloon 40 is in a deflated configuration, graft vessel 20 can be punctured by a needle to perform, for example a hemodialysis. When the dialysis session is finished, occlusal balloon 40 can be inflated again by injecting an appropriate fluid through port device 50 and any remaining blood left near access end 44 can be drawn out of this space and replaced with a fluid such as saline solution or any other appropriate biocompatible fluid.

In its inflated configuration, occlusal balloon 40 is filled with a fluid that causes, or in some embodiments contributorily causes, the expansion within elastic compliance limits of such balloon. In addition, delivery end 42 of occlusal balloon 40 is preferably manufactured to expose the blood flow in blood vessel 10 near anastomosis site 21 to a physiologically active agent such as an anticoagulant agent.

A preferred embodiment of this invention comprises an occlusal balloon which can be repeatedly inflated and deflated within its elastic compliance limits. The occlusal balloon in its inflated configuration effectively seals the graft vessel at the anastomosis site.

In some embodiments of this invention, the fluid injected into the occlusal balloon cannot diffuse out of the occlusal balloon, in which case it is this fluid that directly causes the inflation of the occlusal balloon. An occlusal balloon of this type is herein described as a self-contained occlusal balloon.

In other preferred embodiments of this invention, the occlusal balloon is configured with a semipermeable membrane that allows for fluid transport out of and into the interior is of the occlusal balloon, in which case the fluid injected into the occlusal balloon contributorily causes its initial inflation, with other phenomena, such as osmosis, causing the occlusal balloon to remain in an inflated configuration.

The exposure of the blood in the vessel being accessed to a physiologically active agent can be accomplished, in particular, by delivering into the interior of occlusal balloon 40 a fluid that contains a physiologically active agent, particularly anticoagulants such as heparin at the appropriate dosage, and allowing this heparin to be transported into luminal space 12 of blood vessel 10 across a semipermeable membrane of the adequate porosity that is part of delivery end 42 of occlusal balloon 40. These features and elements of a vascular access device according to this invention function to provide a selective and controlled exposure, and more specifically, to provide a selective and controlled transport.

In this specific exemplary embodiment, this semipermeable membrane preferably allows the flow of aqueous fluid from the blood flow in blood vessel 10 into the interior space of occlusal balloon 40 by osmotic pressure. Osmosis can be accomplished by delivering into the interior of occlusal balloon 40 a fluid that contains a preferably biocompatible substance that cannot permeate across the membrane through which heparin is delivered. An example of such substance is albumin. The fluid within occlusal balloon 40 thus contributes in providing the adequate conditions for osmosis to take place and hence to the maintenance of occlusal balloon 40 in an inflated configuration as heparin, or some other substance, diffuses from the interior of occlusal balloon 40 into the blood flow in blood vessel 10.

In addition to, or instead of, heparin or another anticoagulant, occlusal balloon 40 of the present invention can be used to deliver a medication, and in particular a medication for a long term treatment of a chronic disease. This medication can also be delivered by letting it diffuse across a permeable membrane at delivery end 42 of occlusal balloon 40. In the exemplary embodiment shown in FIG. 1, heparin and any other substance that diffuses through a semipermeable membrane at delivery end 42 can be periodically supplied to the interior space of occlusal balloon 40 by injection through port device 50.

In the practice of hemodialysis and also in the prolonged delivery of medicine for the treatment of a chronic disease, the occlusal balloon of this invention typically contains an aqueous solution that includes a high molecular weight substance that cannot diffuse through the pores of the chosen semipermeable membrane and at least one physiologically active agent of a smaller molecular weight that can diffuse through the pores of the chosen semipermeable membrane. As indicated in the discussion of the embodiment shown in FIG. 1, the preferred high molecular weight substance is albumin and the preferred physiologically active agent is typically heparin.

In some of the embodiments of this invention, heparin is the physiologically active agent and also the solute whose concentration gradient gives rise to the osmotic pressure that keeps the occlusal balloon inflated. The occlusal balloon holds in these embodiments a relatively large volume of solution so that the concentration of heparin does not decrease too rapidly as a consequence of its diffusion rate across the properly chosen semipermeable membrane.

The aqueous solution of albumin and heparin provides the concentration gradient driving the osmotic process which in turn keeps the occlusal balloon in an inflated configuration. Osmosis in this context involves the diffusion of aqueous fluid from the blood in the blood vessel being accessed into the interior of the occlusal balloon through the pores of an appropriately selected semipermeable membrane that is in contact with the blood flow at the anastomosis site. Albumin used in this invention is preferably human albumin with a molecular weight of approximately 65000.

Heparin diffusers through the pores of such semipermeable membrane into the blood in the blood vessel which is being accessed, thus preventing the coagulation of blood that might otherwise take place as a consequence of a variety of factors that are associated with the features of the anastomosed structures. The molecular weight of the heparin preferably used in embodiments of the present invention ranges from about 500 to about 18000. Heparin inhibits reactions that lead to the clotting of blood and the formation of fibrin clots both in vitro and in vivo. The clinical pharmacology of heparin is that of a substance that acts at multiple sites in the normal coagulation system. In particular, small amounts of heparin in combination with antithrombin III (heparin cofactor) can inhibit thrombosis by inactivating activated Factor X and inhibiting the conversion of prothrombin to thrombin. Once active thrombosis has developed, larger amounts of heparin can inhibit further coagulation by inactivating thrombin and preventing the conversion of fibrinogen to fibrin. It is reported that heparin also prevents the formation of a stable fibrin clot by inhibiting the activation of the fibrin stabilizing factor.

In choosing the appropriate concentrations of albumin and heparin, however, a variety of determining factors have to be taken into consideration. Heparin and albumin associate to some extent. This association leads to the effective sequestering of heparin that is not available to diffuse into the blood stream. In addition, some of the albumin can be adsorbed on the semipermeable membrane, thus decreasing the effective concentration of albumin that influences osmosis.

The concentration of albumin is accordingly determined so that the osmotic pressure is comparable to and slightly greater than the vascular pressure in the blood vessel being accessed. For example, venous pressure is typically in the approximate range of about 5 mmHg to about 15 mmHg, and rarely exceeds 30 mmHg, in which case a venous vascular access according to this invention should preferably provide an albumin solution in the occlusal balloon at an osmotic pressure slightly greater than 30 mmHg, such as in the approximate range of about 35 mmHg to about 45 mmHg.

"Nominal molecular weight pore size membrane" in this context characterizes a semipermeable membrane whose pore size is such that particles whose molecular weight is less than the given nominal molecular weight are able to diffuse through the membrane's pores, whereas substances whose molecular weight is greater than or about equal to the given nominal molecular weight cannot diffuse through the membrane's pores. Unless otherwise indicated, molecular weights given herein are expressed in Daltons; albumin concentration units given herein are expressed as a percentage that refers to mass in grams of albumin in 100 ml of solution, and heparin concentration units are expressed as International Units (IU) heparin per ml of solution.

The preferred membrane used in embodiments of this invention is formed from polyethersulfone and is most preferably the semipermeable material sold as Biomax from Millipore. This semipermeable membrane is available in several nominal molecular weight pore sizes in the range from about 5000 to about 50000. Preferred membranes for embodiments of this invention are characterized by a pore size in the range from about 30000 to about 50000 nominal molecular weight. Among these types of semipermeable membrane, a more preferred type is a membrane with a nominal molecular weight pore size of about 50000.

In general, preferred membranes for embodiments of this invention are ultrafiltration membrane materials. In addition to the Biomax membrane, Millipore provides other membranes such as regenerated cellulose membranes sold as Amicon 4M which has a nominal molecular weight pore size of about 1000 to about 100000, and hydrophilic polysulfone membrane sold as Amicon Zm which has a nominal molecular weight pore size of about 500 to about 500000.

Generally, semipermeable membrane base materials include polymeric materials such as polytetrafluoroethylene, polysulfone, polyamide, polyacrylonitrile, and cuprophane of the adequate pore size, although the hydrophobicity of some polymers requires the treatment of the base material prior to its use as a semipermeable membrane.

Clinical dialyzer materials that can be used in the context of this invention include a cuprophane material sold as CF 15.11 from Baxter Health Care Corp., Deerfield, Ill.; cellulose acetate material sold as COAK 4000 and saponified cellulose ester sold as SCE from Cordis Dow Medical, Miami Lalles, Fla.; polymethylmethacrylate Filtryzer membrane from Toray, Tokyo, Japan; cuprammonium material sold as Rayon from Terumo, Japan; and cuprophane material sold as Hemoflow D3 and polysulfone material sold as Hemoflow 60 from Fresenius A. G., Germany.

Semipermeable membranes used in different embodiments of this invention can be attached to the delivery end of the occlusal balloon with or without a backing that provides structural support, depending on the type of membrane being used. Also, the occlusal balloon material at the delivery end can in some embodiments provide structural support to the semipermeable membrane.

The polyethersulfone membrane used in embodiments of this invention are preferably conditioned prior to its use by immersing it in an albumin solution. For example, by immersing it in a 10% albumin aqueous solution for about one week. Once conditioned, the membrane can be repeatedly used as long as it is not allowed to substantially dehydrate.

FIG. 2 shows another exemplary embodiment of the present invention in which an occlusal balloon is used for sealing the end of the graft vessel at the anastomosis site. Blood vessel 110 is being accessed with the aid of graft vessel 120 that is shown as being anastomosed to blood vessel 110 at anastomosis site 121. Graft vessel 120 houses, in this particular embodiment, occlusal balloon 140 with a delivery end 142 and an access end 144.

To prevent the formation of blood clots, blood flowing in lumen 112 is exposed in the region near to delivery end 142 to an anticoagulant agent that is provided with the aid of occlusal balloon 140. Instead of, or in addition to, an anticoagulant agent, blood flowing in lumen 112 can be exposed to other substances. In this particular embodiment, the substances to which blood is exposed are initially contained in the interior of occlusal balloon 140 and they are delivered into the blood stream at delivery end 142 which is so configured as to allow diffusion transport into the blood stream of substances,: and in particular diffusion of an anticoagulant agent.

Delivery end 142 is specifically configured in the embodiment of this invention shown in FIG. 2 with the occlusal balloon material at delivery end 142 being perforated and adjacent to a suitable semipermeable membrane 143. In this configuration, a substance that is to be delivered into the blood stream can pass through the perforations at delivery end 142, reach semipermeable membrane 143, and diffuse into the blood stream through the pores of semipermeable membrane 143. Instead of perforations, occlusal balloon material can have at delivery end 142 any other feature that performs the same function that is performed by perforations, namely allowing for the passage of fluid from and towards semipermeable membrane 143.

In addition to coagulation, blood flow stagnation in the region near anastomosis site 121 must be minimized and it is preferably avoided. To this end, occlusal balloon 140 is so configured as to be able to seal the anastomosis site in a way such that no significant cavity is formed at anastomosis site 121. As indicated regarding the embodiment shown in FIG. 1, the presence of a cavity or substantially recessed space in this region may lead to blood flow stagnation, clot formation, and, in arteries, formation of unacceptably turbulent blood flow.

Graft vessel 120 is shown in FIG. 2 as being anastomosed to blood vessel 110 which is accessed at anastomosis site 121. Graft vessel 120 has port end 124 which is opposite to anastomosis end 122; port end 124 is in this exemplary embodiment connected to port device 150. Graft vessel 120 and port device 150 are typically located subcutaneously and graft vessel 120 is made of a material such as polytetrafluoroethylene (PTFE) or some other biocompatible self sealing material that can be punctured as schematically shown in FIG. 2 by hypodermic needle 158 or by any other medical device that is ordinarily used to inject fluids in or to draw fluids from a cavity.

Graft vessel 120 as shown in the embodiment depicted in FIG. 2 is preferably provided with an enlarged portion 125 near anastomosis end 122. This enlarged portion provides a recessed space into which delivery end 142 and semipermeable membrane 143 collapse when occlusal balloon 140 is deflated.

The exemplary embodiment of port device 150 shown in FIG. 2 comprises conduit 152 that is connected in fluid communication at one of its ends, access end 144, with occlusal balloon 140. The opposite end of conduit 152 can be externally accessed through a self-sealing aperture 154. This self-sealing aperture can be penetrated by a hypodermic needle or any other medical instrument that is typically used to inject fluid into or to draw fluid from a cavity. As indicated regarding the embodiment shown in FIG. 1, port devices such as port device 150 are common medical devices and hence no detailed structure of the connection of such port device to access end 144 is herein sketched.

As shown in the example depicted in FIG. 2, port end 124 of graft vessel 120 is detachably connected to port device 150 by a pressure device 151. As indicated in the discussion of the embodiment depicted in FIG. 1, pressure device 151 can be embodied by any device that exerts sufficient pressure to maintain the leak proof attachment of graft vessel 120 to port device 150. This leak proof attachment can be accomplished in other embodiments of this invention by other engagements as disclosed in the preceding discussion of the embodiment shown in FIG. 1.

The graft vessel of this invention can be provided with a reinforcement structure in its entire length or in part of its length. An exemplary embodiment of such reinforcement structure is schematically shown in the embodiment depicted in FIG. 2 by reinforcement rings 123. These rings are preferably embedded into the material, for example PTFE, of which graft vessel 120 is made, but they can also be partially embedded or externally disposed on graft vessel 120 and attached thereto. Instead of rings, these reinforcement structures can be embodied by a helical coil, longitudinal features aligned with the longitudinal axis of occlusal balloon 140, longitudinal features that present any one amongst a variety of possible chiral configurations, crisscross stripes, or any other reinforcement pattern that is known to provide structural reinforcement to a flexible, generally cylindrical body. Embodiments of these reinforcement structures are preferably made of plastic. Reinforced PTFE graft material that can be used as graft vessel 120 is sold under the name IMPRA by Bard, under the name MEDOX from Boston Scientific and by W. L. Gore, of Phoenix, Ariz.

Typical embodiments of this invention are configured to be adapted to an anastomosis fenestra of about 4 mm, in which case the internal diameter of the graft vessel is about 6 mm. Embodiments of the graft vessel that are provided with an enlarged portion such as enlarged portion 125 in FIG. 2 are configured so that the internal diameter of the graft vessel's enlarged portion is between about 8 mm and about 9 mm. A typical length of embodiments of the occlusal balloon from its delivery end to this access end is preferably about 2 cm. The length of the graft vessel is preferably chosen so that it provides a plurality of puncture sites.

Operations such as inflation, deflation, and use of the embodiment schematically depicted in FIG. 2 are generally performed as described with,regard to the embodiment shown in FIG. 1.

Embodiments of this invention that are provided with an occlusal balloon are preferably configured in a way such that the access end of the occlusal balloon and the port device are separated by several centimeters. In some embodiments, however, the inflated occlusal balloon can extend up to and be in contact with the port device.

FIG. 3 schematically shows a cross-sectional view along plane 5–5' in FIG. 2 of an embodiment of the port device therein depicted. Elements in the cross sectional view are labelled with the same numbers as the corresponding elements are labelled in FIG. 2.

FIG. 4 shows an exploded perspective view of another embodiment of a port device comprising a body 186, a self sealing plug 182 and means for keeping self sealing plug 182 within body 186 effectively sealing cavity 184. In some embodiments of this invention, self sealing plug 182 is embodied by a sheet of silicone. This means for keeping self sealing plug 182 is embodied in the example shown in FIG. 4 by compression ring 180. Body 186 is provided with connector 188 to establish leak proof fluid communication between cavity 184 and the interior of an occlusal balloon. A passage, such as passage 190, is configured for effectively establishing fluid communication between cavity 184 and the interior of an occlusal balloon attached to connector 188. This connector is in some embodiments provided with features such as flanges or ridge 192 for assisting in establishing leak proof communication with an occlusal balloon.

Figure 5:
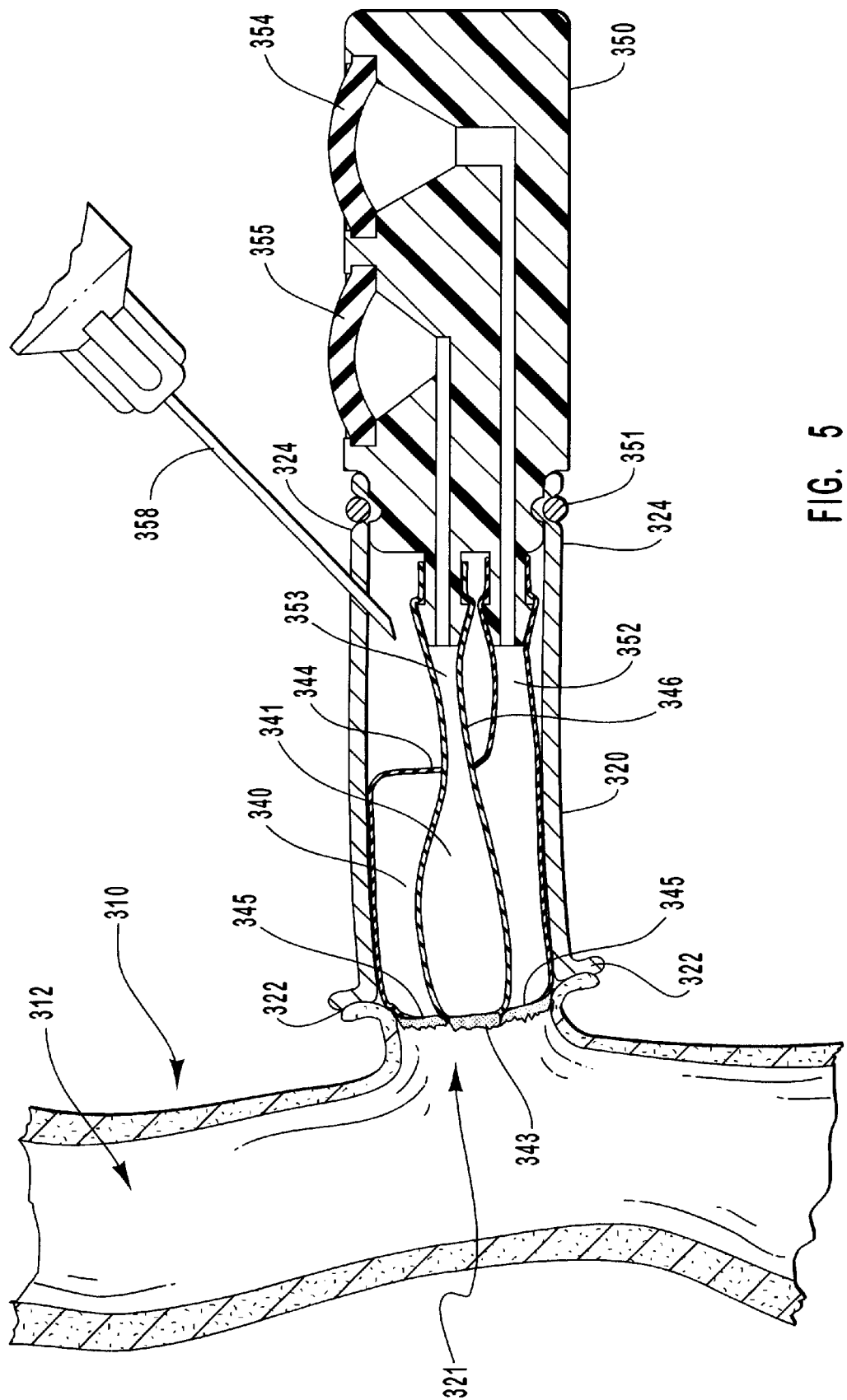
FIG. 5 is a partial cross sectional view of an embodiment of a vascular access system with two occlusal balloons, two semipermeable membranes, and a graft vessel with an enlarged portion.

Some embodiments of this invention may be provided with more than one occlusal balloon. FIG. 5 shows another exemplary embodiment of the present invention which is provided with two occlusal balloons 340 and 341.

Blood vessel 310 is being accessed with the aid of graft vessel 320 that is shown in FIG. 5 as being anastomosed to blood vessel 310 at anastomosis site 321. Graft vessel 320 houses in this particular embodiment first occlusal balloon 340 with first delivery end 345 and first access end 344, and second occlusal balloon 341 with second delivery end 343 and second access end 346.

Blood flowing in lumen 312 is exposed in the region near to delivery ends 343 and 345 to agents that are provided with the aid of occlusal balloons 340 and 341. When more than one agent is to be provided, the range of molecular weights of such agents may be so broad that a single membrane might not be adequate for the diffusion of the different agents into the blood stream. Even if a single membrane were adequate, conditions to be satisfied regarding the replacement, mixing and compatibility of the agents might require that they be kept in different occlusal balloons. In the arrangement shown in FIG. 5, for example, occlusal balloon 340 may contain an aqueous solution of albumin and heparin. Heparin would be delivered into the blood stream by diffusion across a semipermeable membrane at delivery end 345 and the balloon would be kept inflated by osmotic pressure due to the diffusion of an aqueous fluid across the same membrane into the interior of occlusal balloon 340. Occlusal balloon 341 could contain a solution of one or more physiologically active agents, such as medications, that would be delivered into the blood stream by diffusion across a semipermeable membrane at delivery end 343.

The embodiment shown in FIG. 5 and equivalents thereof are preferred embodiments for long term peripheral vascular access, particularly for venous access for parenteral medication. Membrane 343 in these embodiments is suitable for allowing slow diffusion of small molecular weight solutes, such as medication that requires parenteral administration, including antibiotics, small peptides, and hormones.

Delivery ends 343 and 345 of occlusal balloons 340 and 341 are so configured as to be able to seal the anastomosis site in a way such that no significant cavity is formed at anastomosis site 321. As indicated regarding the embodiment shown in FIGS. 1 and 2, the presence of a cavity or substantially recessed space in this region would lead to blood flow stagnation or to the formation of unacceptably turbulent blood flow, both of which would be expected to predispose to thrombosis.

Graft vessel 320 is shown in FIG. 5 as being anastomosed to blood vessel 310 which is accessed at anastomosis site 321. Graft vessel 320 has port end 324 which is opposite to anastomosis end 322; port end 324 is in this exemplary embodiment is connected to port device 350. Graft vessel 320 and port device 350 are typically located subcutaneously and graft vessel 320 is made of a material such as polytetrafluoroethylene (PTFE) or some other biocompatible self sealing material that can be punctured as schematically shown in FIG. 5 by hypodermic needle 358 or by any other medical device that is ordinarily used to inject fluids in or to draw fluids from a cavity.

As indicated in the discussion regarding the exemplary embodiment shown in FIG. 2, graft vessel 320 may have an enlarged portion near anastomosis end 322 like enlarged portion 125 shown in the embodiment depicted in FIG. 2. Such an enlarged portion provides a recessed space for accommodating collapsing delivery ends 343 and 345 as occlusal balloon 340 is deflated. Deflation of occlusal balloon 340 is accompanied when necessary by deflation of occlusal balloon 341.

The exemplary embodiment of port device 350 shown in FIG. 5 comprises conduits 352 and 353. One of the ends of conduit 352 is in fluid communication with occlusal balloon 340 and the opposite end can be externally accessed through self-sealing aperture 354. Analogously, one of the ends of conduit 353 is in fluid communication with occlusal balloon 341 and the opposite end can be externally accessed through self-sealing aperture 355. Self-sealing apertures 354 and 355 can be penetrated by a hypodermic needle or any other medical instrument that is typically used to inject fluid into or to draw fluid from a cavity. Self-sealing apertures 354 and 355 may be arranged relative to each other in port device 350 in a variety of ways. For example, they can be located next to each other and aligned on the same side of port device 350 as shown in FIG. 5, or they can be located at any desired angle relative to each other and facing along different axial directions. As indicated regarding the embodiments shown in FIGS. 1 and 2, port devices such as port device 350 are common medical devices and hence no detailed structure of the connection of such port device to access ends 344 and 346 is herein sketched.

It is understood that configurations of balloons 340 and 341 that depart from that shown in FIG. 5 while including the basic elements therein shown are within the scope of this invention. For example, access ends 344 and 346 can in some embodiments be flush with respect to each other, or balloon 341 can in some embodiments be contained within balloon 340. In other embodiments, balloons 340 and 341 are placed within the graft vessel essentially next to each other, in which case the balloon that is located closer to the port device preferably has an elongated delivery end that extends substantially up to the anastomosis site. Either one of access ends 344 or 346, or both access ends, can in some embodiments extend back to port device 350 and be in contact engagement with such port device, particularly in the inflated configuration. In still other embodiments, balloon 341 can be predominantly located in the space between access end 344 and port device 350, a configuration that would be preferred if balloon 341 had to be subject to, for example, special pressure conditions. In this latter case, an additional conduit, not shown in FIG. 4, would establish fluid communication between the delivery end of balloon 341 and membrane 343. Whether including only one occlusal balloon or a plurality of balloons, the foregoing features describe a variety of embodiments of this invention. In addition, the access end of one or the access ends of several balloons of some embodiments of this invention can be directly connected to port device 350 either in the form of an integral attachment, a detachable connection, or by bonding, such as by adhesive bonding. These embodiments are particularly suitable when any portion of the conduit connecting an access end of a balloon with a self-sealing aperture in the port device has to be eliminated.

Port devices according to this invention can also be embodied by port devices that have additional ports for conventional uses, such as ports that are configured to operate probes, sampling devices, imaging devices and imaging device elements, or medical intervention assisting devices.

As shown in the example depicted in FIG. 5, port end 324 of graft vessel 320 is detachably connected to port device 350 by a pressure device 351 that exerts sufficient pressure to maintain the attachment of graft vessel 320 to port device 350 leak proof. The pressure device 351 is preferably an embodied by an O-ring. As noted in the description of the embodiments shown in FIGS. 1 and 2, this leak proof attachment can be embodied by a threaded engagement, a snap joint engagement, a bound engagement, in particular an adhesive bound engagement, or by any type of leak proof engagement that is well known in the art.

Figure 6A:
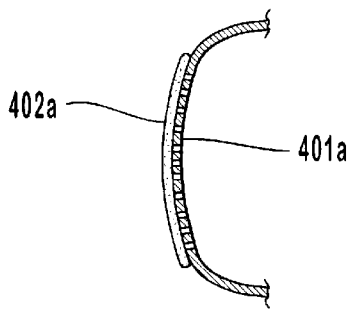
FIGS. 6A–6D schematically illustrate different configurations of a semipermeable membrane at the delivery end of an occlusal balloon.
Figure 6B:
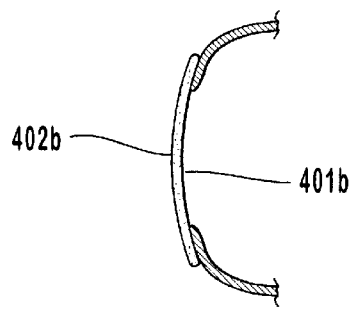
Figure 6C:
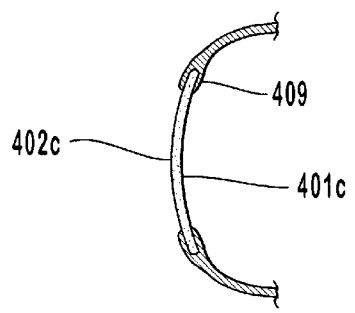

The semipermeable membrane in embodiments of this invention that allow for diffusion of matter into the blood stream can be attached to an occlusal balloon in a variety of configurations. Three examples of such configurations are shown in FIGS. 6A–6C. FIG. 6A depicts a configuration like that of the embodiment shown in FIG. 1, where occlusal balloon material at the delivery end 401a is punctured, perforated, or its structure is such that it allows for the passage of fluid across it so that it is the semipermeable membrane 402a that determines which species diffuse across it into and from the blood stream. In a preferred configuration shown in FIG. 6B, occlusal balloon material at delivery end 401b is provided with a window that generally corresponds with a functional portion of semipermeable membrane 402b. In another configuration shown in FIG. 6C, occlusal balloon material at delivery end 401c is provided with features 409 that brace the edges of semipermeable membrane 402c.

The interior of the occlusal balloon of this invention is in fluid communication with the self-sealing aperture in the port device through an essentially leak-proof connection. This connection is achieved in any of the forms known in the art. Consequently, the detailed features shown in the accompanying Figures pertaining to this connection are merely exemplary and they are not to be regarded as descriptive of a unique way of achieving such connection.

Some embodiments of this invention are provided with a graft vessel that has enlarged portion 125 for housing the collapsed balloon as shown by the phantom lines in FIG. 2. This configuration, or any other equivalent configuration, reduces any possible impediment to the blood flow through the graft vessel that could otherwise be caused by the deflated balloon. Although enlarged portion 125 is not shown for the sake of clarity in the illustrations of the embodiments shown in FIGS. 1 and 5, these and any other embodiment of this invention, can optionally be provided with such enlarged portion of the graft vessel.

Figure 6D:
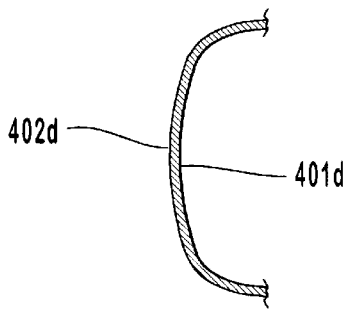

FIG. 6D schematically shows a portion of an embodiment of an occlusal balloon in which semipermeable membrane 402d is integrally formed in occlusal balloon material at delivery end 401d. In one embodiment of this invention, the occlusal balloon is made of, for example, PTFE that is impermeable to the solvent and solute or solutes in the occlusal balloon, and the delivery end of the balloon is made of porous PTFE that embodies semipermeable membrane 402d.

In addition to single layer and bi-layer configurations described above for the disposition of the semipermeable membrane at the delivery end of the occlusal balloon, other configurations are also possible. These additional configurations include a tri-layer configuration and configurations in which the semipermeable membrane is sandwiched between two layers of material, one at each side of the membrane, that allow for the passage of fluid from and to the membrane.

Preferably, the shape of the functional portion of the semipermeable membrane used in some embodiments of this invention is generally circular, in which case corresponding features at the delivery end of the occlusal balloon are also generally circular. These shapes, however, are not unique or determinative of the characteristics and functions of the vascular access device of this invention, and other geometrical shapes can also be used, particularly when the base materials or manufacturing tools can more efficiently be used with noncircular membranes.

The occlusal balloon of specific embodiments of this invention at its delivery end and the membrane or membranes therein located present a generally curved surface that slightly protrudes out of the occlusal balloon's body. This generally curved surface is preferably convex on the side exposed to the blood stream of the blood vessel being accessed. This preferred shape is consistent with the slightly greater pressure within the occlusal balloon relative to the vascular pressure in the blood vessel being accessed by an embodiment of a device according to this invention.

Figure 7A:
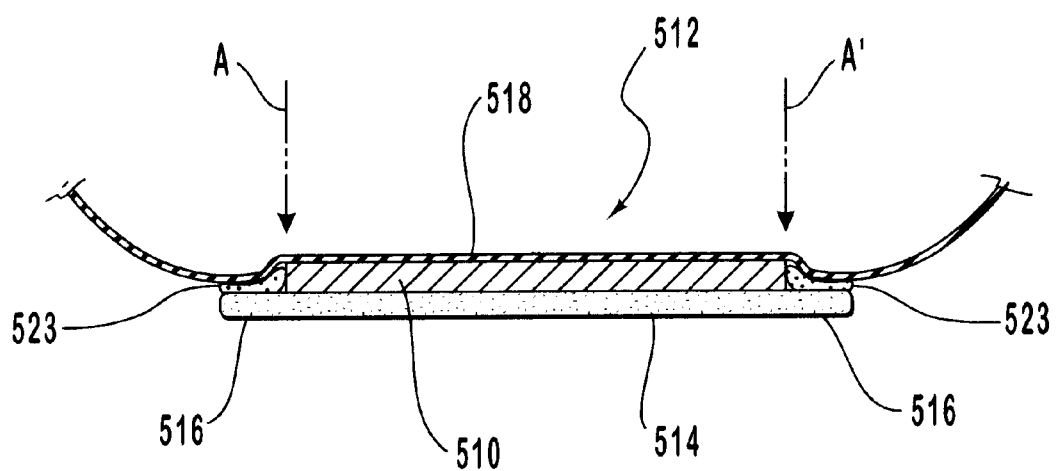
FIGS. 7A–7B schematically illustrate several steps in a technique to attach a semipermeable membrane to the delivery end of an occlusal balloon.
Figure 7B:
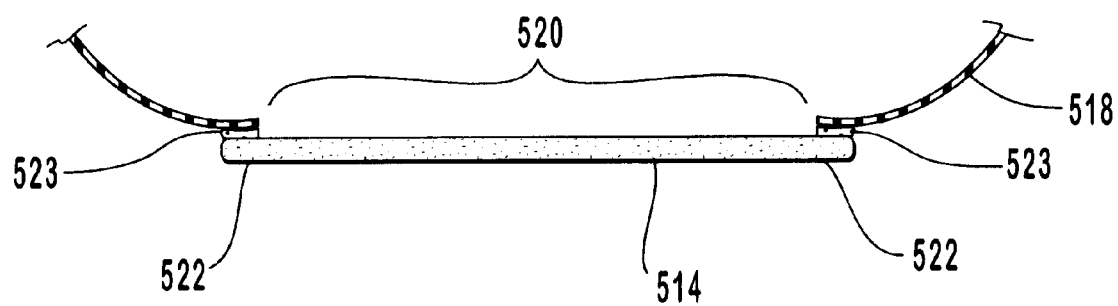

Although a variety of techniques can be relied on to attach a semipermeable membrane to the delivery end of an occlusal balloon as shown in FIG. 6B, a preferred technique comprises the steps of placing a protective material 510 between occlusal balloon delivery end 512 and semipermeable membrane 514 and bonding, preferably with a biocompatible adhesive, contour 516 of semipermeable membrane 514 to the terminal end of the occlusal balloon as schematically shown in FIG. 7A. Occlusal balloon material 518, which may be formed from expandable material such as silicone or latex, is subsequently cut as indicated by broken arrows A–A', thus obtaining the type of configuration shown in FIG. 7B, where functional region 520 of the semipermeable membrane is typically surrounded by small nonfunctional portions 522 bound to the occlusal balloon material.

Although preferred embodiments of occlusal balloons according to this invention include a semipermeable membrane that allows for transport and is part of the osmosis that keeps the occlusal balloon inflated, other embodiments of the occlusal balloon do not include any semipermeable membrane. For example, some embodiments of the occlusal balloon are inflated by the injection of a fluid that is kept within the balloon while it is inflated, with no osmosis contributing to its distension. These embodiments are configured so that the exposure to a physiologically active agent of the blood in the vessel being accessed is accomplished by merely subjecting the blood stream to contact with the agent rather than by relying on diffusion across a membrane and subsequent diffusion in the blood stream. The effects of this contact are predominantly in situ or local effects. These type of occlusal balloons are self-contained occlusal balloons.

When the physiologically active agent is heparin, in situ prevention of clot formation is preferably achieved by subjecting the blood stream to contact with heparin in a heparin immobilizing biocompatible material at the delivery end of the self-contained occlusal balloon. Heparin immobilizing materials include polyvinyl alcohol; surface-modified polymeric biomaterials with poly(ethylene oxide), albumin, and heparin; derivatized dextrins; polymers with hydrophilic spacers; vinyl-pyridine-grafted styrene-butadiene-styrene triblock copolymer; and dimethyl-amino-ethyl-methacrylate-grafted styrene-butadiene-styrene triblock copolymer.

Furthermore, a multifunctional thrombo-resistant coating can be incorporated on the delivery end of an occlusal balloon. This coating includes a siloxane surface onto which a plurality of amine functional groups have been bonded.

Covalently bonded to the amine functional groups are a plurality of poly(ethylene oxide) chains, such that a single poly(elthylene oxide) chain is bonded to a single amine functional group. A plurality of different bioactive molecules, designed to counteract specific blood-material incompatibility reactions, are covalently bonded to poly (ethylene oxide) chains, such that a single bioactive molecule is coupled to a single poly(ethylene oxide) chain. Methods of manufacturing these materials have been previously described. See, for example, International Patent Applications Nos. PCT/US89/01853 and PCT/US91/02415, which are herein incorporated by reference in their entirety. The resulting siloxane that is so manufactured contains a plurality of different bioactive molecules capable of reacting with blood components which come in proximity to the siloxane surface in order to resist blood-material incompatibility reactions.

In the preferred embodiments of the occlusal balloon of this invention with a semipermeable membrane, the physiologically active agent is effective at the release site, namely in situ. The dosage can be regulated so that the active agent is effective systemically because the active agent circulates with the blood stream. This type of sources of physiologically active agents are herein described as permeating sources of physiologically active agents, and they include embodiments such as those shown in FIGS. 6A–6D. The dose required to achieve the anticoagulant effect locally is much less than a systemically therapeutic dose, thus the long term risk associated with in situ effects is less than the risk associated with full systemic anticoagulation.

When the physiologically active agent is provided by immobilizing it on a self-contained occlusal balloon, the active agent is predominantly effective in situ, at or near the contact site. Such sources of physiologically active agents are herein described as in-situ sources of physiologically active agents. They include embodiments of the delivery end of an occlusal balloon on which the physiologically active agent is attached at the outer surface that is exposed to the blood flow.

In addition, other embodiments of this invention incorporate a self-contained balloon that provides a source of at least one physiologically active agent whose effects are manifested in situ and systemically without transport across a semipermeable membrane. In these embodiments, the physiologically active agent is typically released by a substance that is incorporated on the delivery end of the occlusal balloon that is exposed to the blood flow. Such sources of physiologically active agents are herein described as non-permeating sources of physiologically active agents. For example, when the physiologically active agent is an anticoagulant, nitrogen oxide releasing polymers can be incorporated on the delivery end of the occlusal balloon so that NO is released into the blood stream. Examples of NO-releasing polymers include diazeniumdiolates added to plastics such as polyvinylchloride and polyurethane. In this case, diazeniumdiolates include specific compounds such as sodium 1-(N,N-diethylamino)diazen-1-ium-1,2-diolate, disodium 1-[2(S)carboxylatopyrrolidin-1-yl]diazen-1-ium-1,2-diolate, sodium 1(piperazin-1-yl)diazen-1-ium-1,2-diolate, and 1-{N-methyl-N-[6-(Nmethylammonio)hexyl]amino}diazen-1-ium-1,2-diolate.

The features of each one of the herein described embodiments of the occlusal balloon are not meant to be exclusive of features of other embodiments that can be incorporated in the same occlusal balloon to render a functional combination. For example, an occlusal balloon with a semipermeable membrane can also incorporate a source of a physiologically active agent for predominantly in-situ effects, and/or incorporate a source of a physiologically active agent for in situ and systemic effects of the type described in relation to embodiments of self-contained occlusal balloons.

A vascular access with a system according to this invention is preferably created by first performing a vascular anastomosis to attach a graft vessel to the blood vessel that is being accessed, and then placing an occlusal balloon within the graft vessel. This occlusal balloon may be provide with a port device already attached to it, or the port device may be subsequently attached to the occlusal balloon by conventional techniques. Once a vascular access system according to this invention is placed at the access site, the entire system preferably remains subcutaneously placed for its use in procedures such as dialysis, in particular hemodialysis, and drug delivery. In addition to hemodialysis, other example of useful external blood treatments that can be performed with the present invention include plasmapheresis, cytopheresis, hemodialysis, apheresis, hemoperfusion, and hemofiltration. Examples of such external treatment methods are provided in greater detail in U.S. patent application Ser. No. 09/481,283 entitled Methods for External Treatment of Blood filed on Jan. 11, 2000, which is hereby incorporated by reference.

It is understood that elements of any embodiment of the vascular access system according to this invention may be provided with suitable radio-opaque markings so that its location or particular configuration can be externally observed. This markings can be particularly useful when incorporated in the vascular graft or in the occlusal balloon.

Examples of use of Occlusal Balloons

Figure 8:
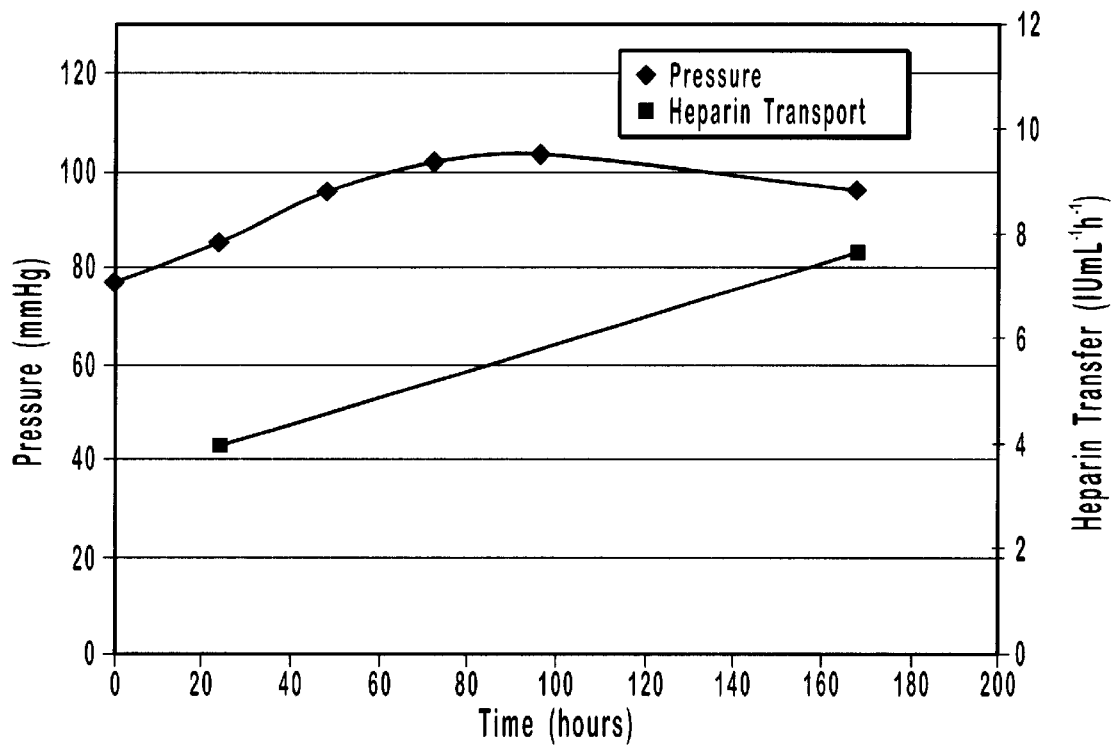
FIG. 8 shows the time evolution of the osmotic pressure and the osmotic pressure and heparin transfer for a heparin aqueous solution with no albumin.
Figure 9:
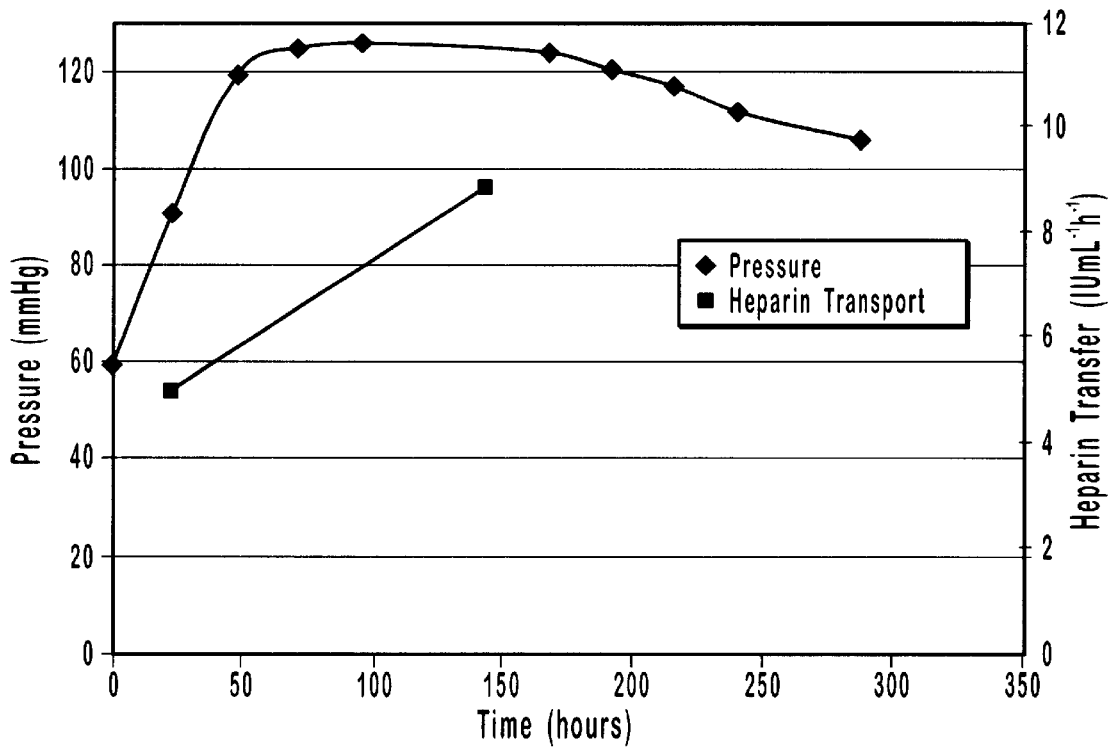
FIG. 9 shows the time evolution of the osmotic pressure and the osmotic pressure and heparin transfer for a heparin aqueous solution with 1% albumin.

FIGS. 8 and 9 show pressure and heparin transfer as a function of time as experienced by an embodiment of a permeable balloon according to the present invention. In these experiments, solutions of heparin were used at concentrations up to about 20000 IU. Solutions of albumin were used at concentrations of up to about 5%. Commercial availability of the respective solutions of heparin and albumin determined the choice of these upper concentration limits.

Osmotic pressures were measured with a pressure transducer. The use of this device instead of liquid column height measurements reduces or even avoids errors that are associated with the use of liquid columns. These errors are typically associated with factors such as solute concentration inhomogeneity problems or frictional problems that can lead to incorrect pressure readings.

Solutions with heparin at different concentrations were used in successive experiments with embodiments of a permeable balloon. In some experiments, the solutions contained albumin, whereas in other experiments no albumin was present. FIGS. 8 and 9 illustrate results obtained in experiments performed with a heparin solution with no albumin (FIG. 8), and with a heparin solution with 1% albumin (FIG. 9). In embodiments with solutions that contained heparin only, the osmotic pressure is due to the heparin that remains in the balloon, whereas in embodiments with heparin and albumin solution, the osmotic pressure is due to the albumin and to the heparin that remains in the balloon. The data shown in FIGS. 8 and 9 were obtained with Millipore 50 as semipermeable membrane, and with 20000 IU/ml heparin solutions.

As shown in FIG. 8, osmotic pressure of almost 80 mmHg was measured shortly after the heparin solution was placed in a permeable balloon. The pressure remained above 80 mmHg for over 150 h, and remained at or about 100 mmHg for at least 120 h. Heparin transfer rates were about 4 IU $ml^{-1}$ $h^{-1}$ one day after the solution was placed in the balloon, and about 7.7 IU $ml^{-1}$ $h^{-1}$ about 170 h after the solution was placed in the balloon.

FIG. 9 shows that a peak pressure of over 120 mmHg was obtained with a solution that contained heparin and 1% albumin. This observation should be expected because in this case albumin, which does not significantly permeate through the membrane, causes osmotic pressure in addition to the heparin that remains within the balloon. Heparin transfer rates were about 5 IU $ml^{-1}$ $h^{-1}$ one day after the solution was placed in the balloon, and almost 9 IU $ml^{-1}$ $h^{-1}$ about 150 h after the solution was placed in the balloon.

These heparin transfer rates are adequate in light of desirable transport rates in the range of about 5 IU $ml^{-1}$ $h^{-1}$ to about 10 IU $ml^{-1}$ $h^{-1}$. These transport rates from a balloon whose volume is about 2 ml lead to the intravenous administration of not more than 500 IU heparin per day, or to the administration of not more than 5000 IU heparin in a ten-day period.

Safety measures, in addition to practical factors, determine the preferred size of embodiments of permeable balloons of this invention. The administration of at most about 20000 IU heparin in a single administration is currently regarded as an acceptable risk. The amount of heparin that would be suddenly delivered upon rupture of a 5 ml balloon right after having been filled with heparin solution at a concentration of 20000 IU/ml would be about 100000 IU. Instead, this amount would be about 20000 IU if a 2 ml balloon were filled with 10000 IU/ml heparin. Consequently, a 2-ml balloon is preferred in most embodiments of permeable balloons.

The transport rates shown in FIGS. 8–9 also indicate each supply of heparin within the balloon can intravenously provide heparin for at least a ten-day period before the balloon is recharged with a fresh supply of heparin. The pressure data shown in the same FIGS. show that sufficiently high pressure can be achieved with embodiments of the present invention because even in unusual conditions the venous pressure does not rise above 50 mmHg.

The foregoing procedure to determine osmotic pressure and concentrations of substances in the fluid filling of an embodiment of an occlusal balloon according to this invention can be properly adapted with ordinary skill in the art to analogously determine the osmotic pressure and adequate concentrations of other substances in the same or in a different type of vascular access.

Summary of Preferred Embodiments

The elements of the embodiments of this invention disclosed hereinabove, equivalents thereof, and their functionalities can be expressed as means for performing specified functions as described hereinbelow.

Many examples are provided herein of a means for selectively occluding an opening in a blood vessel. Examples of means for selectively occluding an opening according to this invention include: occlusal balloons such as self-contained occlusal balloons, occlusal balloons with a semipermeable membrane such as balloon 140 in FIG. 3, occlusal balloons with radio-opaque markings, occlusal balloons that are inflated with a liquid, occlusal balloons that are inflated with a gas, and occlusal balloons that are configured to operate in conjunction with or in the presence of at least another occlusal balloon, such as occlusal balloons 340, 341 in FIG. 5. Occlusal balloon 40 in FIG. 1 illustrates an exemplary embodiment of a self-contained occlusal balloon when delivery end 42 does not essentially allow for significant matter transport. Occlusal balloon 40 in FIG. 1 illustrates an exemplary embodiment of an occlusal balloon with a semipermeable membrane when delivery end 42 allows for selective matter transport.

Note that each embodiment of the means for selectively occluding an opening according to this invention has a delivery end that is generally located in the region near the anastomosis site and an opposite access end that is typically provided with a connection to the means for selectively providing access to a means for selectively occluding an opening. Each embodiment of a means for selectively occluding an opening in a blood vessel functions according to this invention by adopting a variety of configurations such as a distended configuration and a contracted configuration. In particular, the distended configuration can be an inflated configuration, and the contracted configuration can be a collapsed configuration. Preferably, the distended configuration is adopted when an embodiment of a means for selectively occluding an opening is filled with a liquid, although the fluid filling some of such embodiments can also be a gas. Blood from the accessed vessel cannot infiltrate into the anastomosed graft vessel when the embodiment of the means for selectively occluding an opening is in its distended configuration, whereas fluid communication from the interior of the anastomosed graft vessel into the lumen of the accessed blood vessel is allowed in the contracted configuration of the same embodiment. Any of such specific embodiments is manufactured so that it can change from any one of these particular configurations to the other and vice-versa a plurality of times. The number of times which these changes in configuration are experienced by embodiments of the means for selectively occluding an opening according to this invention can be of the order of the number of injections that a blood vessel would typically be subjected to during a long term treatment of a chronic affliction or during dialysis treatment.

Many examples are also provided herein of a means for selectively providing access to a means for selectively occluding an opening in a blood vessel. Examples of means for selectively providing access to a means for selectively occluding an opening in a blood vessel include: port devices such as a port device with one self-sealing access cavity, such as port devices 50 shown in FIG. 1 and port device 150 shown in FIGS. 2–3, a port device with a plurality of self-sealing access cavities, such as port device 350 shown in FIG. 5, and a port device that includes ports for providing conduits to operate probes, sampling devices, imaging devices and imaging device elements, or medical intervention assisting devices.

Each embodiment of the means for selectively providing access to a means for selectively occluding an opening facilitates the external introduction into or the extraction from a specific embodiment of the means for selectively occluding an opening of fluid therein contained. In particular, an embodiment of the means for selectively providing access to a means for selectively occluding an opening is adapted for a subcutaneous placement and it is provided with at least one self-sealing cavity for selectively allowing fluid communication through a conduit into the access end of an embodiment of a means for selectively occluding an opening in a blood vessel.

Examples are also provided herein of a means for selectively and controllably exposing blood flow to an agent in a vascular access. Means for selectively and control lably exposing blood flow to an agent according to this invention is embodied by means for selectively effectuating transport of an agent in a vascular access, and by means for selectively subjecting blood flow to contact with an agent. Exemplary embodiments of each one of these means are enumerated in turn below.

Means for selectively effectuating transport of an agent in a vascular access according to this invention is embodied by permeating sources of agents such as physiologically active agents. These permeating sources are more specifically embodied by sources such as a semipermeable membrane, exemplified by semipermeable membranes 143 shown in FIG. 3, 402*a* shown in FIG. 6A, 402*b* shown in FIG. 6B, 402*c* shown in FIG. 6C, and 402*d* shown in FIG. 6D; sources that include a plurality of semipermeable membranes, exemplified by semipermeable membranes 343 and 345 shown in FIG. 5, semipermeable membranes in any of a mono-layer, bi-layer, tri- or generally multi-layer and sandwiched configurations; sources that include at least a semipermeable membrane with a backing (membrane mounting by backing); sources that include at least a semipermeable membrane braced to an embodiment of means for selectively occluding an opening (membrane mounting by bracing), exemplified by the embodiment shown in FIG. 6C; sources that include at least a semipermeable membrane bonded to an embodiment of means for selectively occluding an opening (membrane mounting by bonding), exemplified by the embodiment shown in FIG. 6B; sources that include at least a semipermeable membrane that is backed by material of an embodiment of means for selectively occluding an opening (membrane mounting by backing), exemplified by the embodiment shown in FIG. 6A; and sources that include a semipermeable region of material of an embodiment of means for selectively occluding an opening, exemplified by the embodiment shown in FIG. 6D.

Each embodiment of a means for selectively and controllably exposing blood flow to an agent in a vascular access is integrally formed in or attached to the delivery end of an embodiment of a means for selectively occluding an opening according to this invention. The means for selectively and controllably exposing blood flow to an agent in a vascular access functions according to the present invention by exposing the blood flow at the anastomosis site to at least one physiologically active agent, such as a substance that will prevent the formation of blood clots. Means for selectively and controllably subjecting blood flow to contact with an agent according to this invention is embodied by in-situ sources of physiologically active agents and by nonpermeating sources of physiologically active agents.

The anastomosed graft of this invention provides physical support to a particular embodiment of the means for selectively occluding an opening and to a particular embodiment of the means for selectively providing access to a means for selectively occluding an opening. In preferred embodiments, this support is provided by a housing such that the anastomosed graft contains in its interior an embodiment of a means for selectively occluding an opening which has attached thereto an embodiment of a means for selectively exposing blood flow to an agent in the vascular access.

One of the ends of the anastomosed graft of this invention is anastomosed to the vessel being accessed. The opposite end of the anastomosed graft is integrally or detachably connected to an embodiment of means for providing access to a means for selectively occluding an opening.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by united states letters patent is:

1. A vascular access system for facilitating repeated access to a blood vessel, the system comprising:
    (a) a graft vessel having an anastomosis end,
    (b) means for selectively occluding an opening in a blood vessel after anastomosis of the graft vessel to a blood vessel, wherein said occluding means is positioned and adapted to expand within the graft vessel at the anastomosis end of the graft vessel to block fluid communication between the graft vessel and the blood vessel, wherein said occluding means is adapted to contract to enable selective fluid communication between the graft vessel and the blood vessel; and
    (c) means for selectively providing access to the occluding means, wherein said means for selectively providing access is in fluid communication with said occluding means, and wherein said graft vessel extends in a leak-proof manner from the means for selectively providing access such that the occluding means can be selectively distended and contracted as fluid is delivered and withdrawn via the means for selectively providing access after anastomosis of the graft vessel to the blood vessel;
        wherein said vascular access system is sized and adapted to remain subcutaneously positioned in a patient's body after anastomosis of the graft vessel to the blood vessel to enable selective fluid communication between the graft vessel and the blood vessel to be achieved by accessing the means for selectively providing access through the patient's skin.

2. A vascular access system for facilitating repeated access to a blood vessel as recited in claim 1, further comprising:
    means for selectively and controllably exposing blood flow in a blood vessel to at least one physiologically active agent at the delivery end of the means for selectively occluding an opening.

3. A vascular access system as recited in claim 2, wherein said means for selectively and controllably exposing blood flow in the blood vessel is integrally formed to a delivery end of said means for selectively occluding an opening.

4. A vascular access system as recited in claim 2, wherein said means for selectively and controllably exposing blood flow in the blood vessel is attached to a delivery end of said means for selectively occluding an opening.

5. A vascular access system as recited in claim 2, wherein said means for selectively and controllably exposing blood flow in the blood vessel is a means for selectively effectuating transport of an agent from the vascular access system to the blood vessel.

6. A vascular access system as recited in claim 5, wherein said means for selectively effectuating transport of an agent from the vascular access system is at least one semipermeable membrane.

7. A vascular access system as recited in claim 6, wherein said at least one semipermeable membrane is disposed in a configuration selected from the group consisting of a monolayer, a multi-layer, and a laminate with another material.

8. A vascular access system as recited in claim 2, wherein said means for selectively and controllably exposing blood flow in the blood vessel is a means for selectively subjecting blood flow to contact with an agent.

9. A vascular access system as recited in claim 8, wherein said at least one semipermeable membrane includes a semipermeable region of said means for selectively occluding an opening.

10. A vascular access system as recited in claim 8, wherein said means for selectively subjecting blood flow to contact with an agent is an in-situ source of a physiologically effective agent.

11. A vascular access system as recited in claim 8, wherein said means for selectively subjecting blood flow to contact with an agent is a non-permeating source of a physiologically effective agent.

12. A vascular access system as recited in claim 1, wherein said means for selectively providing access is separable from said graft vessel.

13. A vascular access system as recited in claim 1, wherein said means for selectively occluding an opening includes at least one occlusal balloon.

14. A vascular access system as recited in claim 13, wherein said occlusal balloon is a self-contained occlusal balloon.

15. A vascular access system as recited in claim 13, wherein said occlusal balloon prevents significant transport of matter from the interior of said occlusal balloon to the interior of the blood vessel.

16. A vascular access system as recited in claim 1, wherein said means for selectively providing access is a port device.

17. A vascular access system as recited in claim 16, wherein said port device has at least one self-sealing cavity.

18. A vascular access system as recited in claim 16, wherein said port device has at least one port for delivery of a liquid or a gas.

19. A vascular access apparatus for facilitating repeated access to a blood vessel through a graft vessel having port and anastomosis ends and that is anastomosed to the blood vessel at the anastomosis end, the apparatus comprising:
   (a) an occlusal balloon having a delivery end opposite an access end and an interior capable of receiving a fluid, said occlusal balloon being sized to expand within a graft vessel anastomosed to a blood vessel such that said delivery end generally corresponds with the anastomosis end of a graft vessel;
   (b) a port device in fluid communication with the occlusal balloon at the access end of the occlusal balloon, said port device being in fluid communication with said occlusal balloon, and said port device being sized and adapted for leak proof attachment to the port end of a graft vessel; and
   (c) a semipermeable membrane at the delivery end of the occlusal balloon allowing for selective matter transport between the blood in the blood vessel and the interior of the occlusal balloon.

20. A vascular access apparatus as recited in claim 19, wherein said occlusal balloon is configured to adopt a distended configuration and a contracted configuration.

21. A vascular access apparatus as recited in claim 19, further including another occlusal balloon.

22. A vascular access apparatus as recited in claim 19, wherein said occlusal balloon prevents significant transport of matter from the interior of said occlusal balloon to the interior of the blood vessel.

23. A vascular access apparatus as recited in claim 19, wherein said port device has at least one self-sealing cavity.

24. A vascular access apparatus as recited in claim 19, wherein said port device is provided with at least one port for delivery of a liquid or a gas.

25. A vascular access apparatus as recited in claim 19, wherein said semipermeable membrane is integrally formed into the delivery end of said occlusal balloon.

26. A vascular access apparatus as recited in claim 19, wherein said semipermeable membrane is attached to the delivery end of said occlusal balloon.

27. A vascular access apparatus as recited in claim 19, wherein said semipermeable membrane is disposed in a configuration selected from the group consisting of a monolayer, a multi-layer, and a laminate with another material.

28. A vascular access apparatus for facilitating repeated access to a blood vessel through a graft vessel having port and anastomosis ends and that is anastomosed to the blood vessel at the anastomosis end, the apparatus comprising:
   (a) an inflatable balloon having a delivery end opposite, an opposite access end and an interior capable of receiving a fluid, said inflatable balloon being sized to expand within a graft vessel anastomosed to a blood vessel such that said delivery end generally corresponds with the anastomosis end of a graft vessel;
   (b) a port device in fluid communication with the inflatable balloon at the access end of the inflatable balloon, wherein said port device has at least one self-sealing aperture for delivering fluids into or for extracting fluids from the inflatable balloon, and said port device being sized and adapted for leak proof attachment to the port end of a graft vessel; and
   (c) a semipermeable membrane at the delivery end of the inflatable balloon that is impermeable to substances having a nominal molecular weight that is greater than or equal to about 50,000.

29. A vascular access system for facilitating repeated access to a blood vessel, comprising:
   (a) a graft vessel with an anastomosis end;
   (b) means for selectively occluding an opening at the anastomosis end, wherein the occluding means is positioned and adapted to expand within the graft vessel at the anastomosis end of the graft vessel to block fluid communication between the graft vessel and the blood vessel, wherein said occluding means is adapted to contract to enable selective fluid communication between the graft vessel and the blood vessel;
   (c) means for selectively providing access to the occluding means, wherein the means for selectively providing access is in fluid communication with the occluding means and wherein the graft vessel extends in a leak-proof manner from the means for selectively providing access such that the occluding means can be selectively distended and contracted as fluid is delivered and withdrawn via the means for selectively providing access after anastomosis of the graft vessel to the blood vessel; and
   (d) means for selectively and controllably exposing blood flow in the blood vessel to at least one physiologically active agent at the delivery end of the means for selectively occluding an opening; and
      wherein said vascular access system is sized and adapted to remain subcutaneously positioned in a patient's body after anastomosis of the graft vessel to the blood vessel to enable selective fluid communication between the graft vessel and the blood vessel to be achieved by accessing the means for selectively providing access through the patient's skin.

30. A vascular access system as recited in claim 29, wherein said means for selectively providing access is separable from said graft vessel.

31. A vascular access system as recited in claim 29, wherein said means for selectively occluding an opening is an occlusal balloon.

32. A vascular access system as recited in claim 31, wherein said occlusal balloon is a self-contained occlusal balloon.

33. A vascular access system as recited in claim 31, further including another occlusal balloon.

34. A vascular access system as recited in claim 31, wherein said occlusal balloon prevents significant transport of matter from the interior of said occlusal balloon to the interior of the blood vessel.

35. A vascular access system as recited in claim 29, wherein said means for selectively providing access is a port device.

36. A vascular access system as recited in claim 35, wherein said port device has at least one self-sealing cavity.

37. A vascular access system as recited in claim 35, wherein said port device is provided with at least one port for delivery of a liquid or a gas.

38. A vascular access system as recited in claim 29, wherein said means for selectively and controllably exposing blood flow in the blood vessel is integrally formed into the delivery end of said means for selectively occluding an opening.

39. A vascular access system as recited in claim 29, wherein said means for selectively and controllably exposing blood flow in the blood vessel is attached to the delivery end of said means for selectively occluding an opening.

40. A vascular access system as recited in claim 29, wherein said means for selectively and controllably exposing blood flow in the blood vessel is a means for selectively effectuating transport of an agent from the vascular access system to the blood vessel.

41. A vascular access system as recited in claim 40, wherein said means for selectively effectuating transport of an agent from the vascular access apparatus is a semipermeable membrane.

42. A vascular access system as recited in claim 41, wherein said semipermeable membrane is disposed in a configuration selected from the group consisting of a monolayer, a multi-layer, and a laminate with another material.

43. A vascular access system as recited in claim 29, wherein said means for selectively and controllably exposing blood flow in the blood vessel is a means for selectively subjecting blood flow to contact with an agent.

44. A vascular access system as recited in claim 43, wherein said means for selectively subjecting blood flow to contact with an agent is an in-situ source of a physiologically effective agent.

45. A vascular access system as recited in claim 43, wherein said means for selectively subjecting blood flow to contact with an agent is a non-permeating source of a physiologically effective agent.

46. A vascular access system for facilitating repeated access to a blood vessel, comprising:
(a) a graft vessel with an anastomosis end and an opposite port end, the anastomosis end of the graft vessel being adapted for anastomosis to a blood vessel;
(b) an occlusal balloon having a delivery end, an opposite access end and an interior capable of receiving a fluid, and being disposed within the graft vessel in a configuration such that the delivery end of the occlusal balloon generally corresponds with the anastomosis end of the graft vessel;
(c) a port device attached in a leak proof manner to the port end of the graft vessel, wherein the port device is in fluid communication with the occlusal balloon at the access end of the occlusal balloon; and
(d) a semipermeable membrane at the delivery end of the occlusal balloon allowing for selective matter transport between the blood in the blood vessel and the interior of the occlusal balloon.

47. A vascular access system as recited in claim 46, wherein said semipermeable membrane is integrally formed into the delivery end of said occlusal balloon.

48. A vascular access system as recited in claim 46, wherein said semipermeable membrane is attached to the delivery end of said occlusal balloon.

49. A vascular access system as recited in claim 46, wherein said port device has at least one self-sealing cavity.

50. A vascular access system for facilitating repeated access to a blood vessel, comprising:
(a) an inflatable balloon having a delivery end, an opposite access end and an interior capable of receiving a fluid;
(b) a port device in fluid communication with said inflatable balloon at the access end of said inflatable balloon, wherein said port device has at least one self-sealing aperture for delivering, fluids into or for extracting fluids from the inflatable balloon;
(c) a semipermeable membrane at the delivery end of the inflatable balloon that is impermeable to substances having a nominal molecular weight that is greater than or equal to about 50000; and
(d) a graft vessel with an anastomosis end and an opposite port end, the anastomosis end of the graft vessel being configured for anastomosis to a blood vessel, wherein the inflatable balloon is adapted for being disposed within the graft vessel in a configuration such that the delivery end of the inflatable balloon generally corresponds with the anastomosis end of the graft vessel, and wherein the port device is attachable in a leak proof manner to the port end of the graft vessel.

51. A vascular access system for facilitating repeated access to a blood vessel, the system comprising:
(a) a graft vessel with an anastomosis end;
(b) an occlusal balloon positioned and adapted to expand within the graft vessel at the anastomosis end of the graft vessel to block fluid communication between the graft vessel and a blood vessel once the graft vessel is anastomosed to the blood vessel, wherein said occlusal balloon is adapted to contract to enable selective fluid communication between the graft vessel and the blood vessel; and
(c) a port device in fluid communication with said occlusal balloon, wherein said graft vessel extends in a leak-proof manner from the port device such that the occlusal balloon can be selectively distended and contracted as fluid is delivered and withdrawn via the port device after anastomosis of the graft vessel to the blood vessel;
wherein said vascular access system is sized and adapted to remain subcutaneously positioned in a patient's body after anastomosis of the graft vessel to the blood vessel to enable selective fluid communication between the graft vessel and the blood vessel to be achieved by accessing the port device through the patient's skin.

52. A vascular access system as recited in claim 51, wherein said graft vessel and said port device are separable.

53. A vascular access system as recited in claim 51, wherein said graft vessel has a port end, and wherein said port device is attached to the port end of the graft vessel.

54. A vascular access apparatus as recited in claim 51, wherein said occlusal balloon prevents significant transport of matter from the interior of said occlusal balloon to the interior of the blood vessel.

55. A vascular access system as recited in claim 51, wherein said occlusal balloon has a semipermeable membrane at a delivery end of the occlusal balloon adapted to allow selective matter transport between the blood in the blood vessel and the interior of the occlusal balloon.

56. A vascular access apparatus as recited in claim 55, wherein said semipermeable membrane is integrally formed into the delivery end of said occlusal balloon.

57. A vascular access apparatus as recited in claim 55, wherein said semipermeable membrane is attached to the delivery end of said occlusal balloon.

58. A vascular access system as recited in claim 51, wherein said occlusal balloon is adapted to enable heparin to be delivered from the occlusal balloon to the blood vessel.

59. A vascular access apparatus as recited in claim 51, wherein said port device has at least one self-sealing cavity.

60. A vascular access apparatus as recited in claim 51, wherein said port device is provided with at least one port for delivery of a liquid or a gas.

61. A vascular access system for facilitating repeated access to a blood vessel, the system comprising:
 (a) a graft vessel with an anastomosis end opposite from a port end;
 (b) an occlusal balloon having a delivery end, wherein the occlusal balloon is positioned and adapted to expand within the graft vessel at the anastomosis end of the graft vessel to block fluid communication between the graft vessel and a blood vessel once the graft vessel is anastomosed to the blood vessel such that only the delivery end is exposed to blood in the opening of the blood vessel, wherein said occlusal balloon is adapted to contract to enable selective fluid communication between the graft vessel and the blood vessel; and
 (c) a port device coupled with said occlusal balloon to provide fluid communication between said port device and said occlusal balloon while preventing fluid communication, wherein said port device is attached in a leak-proof manner to the port end of the graft vessel such that the occlusal balloon can be selectively distended and contracted as fluid is delivered and withdrawn via the port device after anastomosis of the graft vessel to the blood vessel;
  wherein said vascular access system is sized and adapted to remain subcutaneously positioned in a patient's body after anastomosis of the graft vessel to the blood vessel to enable selective fluid communication between the graft vessel and the blood vessel to be achieved by accessing the port device through the patient's skin.

62. A vascular access system for facilitating repeated access to a blood vessel, the system comprising:
 (a) a graft vessel having an anastomosis end,
 (b) means for selectively occluding an opening in a blood vessel after anastomosis of the graft vessel to a blood vessel, wherein said occluding means is positioned and adapted to expand within the graft vessel at the anastomosis end of the graft vessel to block fluid communication between the graft vessel and the blood vessel, wherein said occluding means is adapted to contract to enable selective fluid communication between the graft vessel and the blood vessel; and
 (c) means for selectively providing access to the occluding means, wherein said means for selectively providing access is in fluid communication with said occluding means, and wherein said graft vessel extends in a leak-proof manner from the means for selectively providing access such that the occluding means can be selectively distended and contracted as fluid is delivered and withdrawn via the means for selectively providing access after anastomosis of the graft vessel to the blood vessel;
  wherein said vascular access system is sized and adapted to remain subcutaneously positioned in a patient's body after anastomosis of the graft vessel to the blood vessel to enable selective fluid communication between the graft vessel and the blood vessel to be achieved by accessing the means for selectively providing access through the patient's skin.
  wherein said vascular access system is configured to enable blood to be withdrawn from the graft vessel by penetrating the patient's skin and the graft vessel with a needle once the occluding means has been contracted.

63. A vascular access system for facilitating repeated access to a blood vessel, comprising:
 (a) a graft vessel with an anastomosis end;
 (b) an occlusal balloon positioned and adapted to expand within the graft vessel at the anastomosis end of the graft vessel to block fluid communication between the graft vessel and a blood vessel once the graft vessel is anastomosed to the blood vessel, wherein said occlusal balloon is adapted to contract to enable selective fluid communication between the graft vessel and the blood vessel; and
 (c) a port device in fluid communication with said occlusal balloon, wherein said graft vessel extends in a leak-proof manner from the port device such that the occlusal balloon can be selectively distended and contracted as fluid is delivered and withdrawn via the port device after anastomosis of the graft vessel to the blood vessel;
  wherein said vascular access system is sized and adapted to remain subcutaneously positioned in a patient's body after anastomosis of the graft vessel to the blood vessel to enable selective fluid communication between the graft vessel and the blood vessel to be achieved by accessing the port device through the patient's skin; and
  wherein said vascular access system is configured to enable blood to be withdrawn from the graft vessel by penetrating the patient's skin and the graft vessel with a needle once the occlusal balloon has been contracted.

* * * * *

UNITED STATES PATENT AND TRADEMARK OFFICE
CERTIFICATE OF CORRECTION

PATENT NO.         : 6,656,151 B1
APPLICATION NO. : 09/480964
DATED                  : December 2, 2003
INVENTOR(S)        : Blatter It is certified that error appears in the above-identified patent and that said Letters Patent is hereby corrected as shown below:

On the Title Page, Item (73)
The name of the Assignee should be --Vital Access Corporation, Salt Lake City, UT (US)-- pursuant to a Merger Agreement recorded on February 7, 2008, at Reel 020468, Frame 0624

Column 2, line 12, ". . . that typically ranges form about 2 . . ." change to --. . . that typically ranges from about 2 . . .--

Column 5, line 24, ". . . example depicted in Figure 11 port end . . ." change to --. . . example depicted in Figure 1, port end . . .--

Column 6, line 19, ". . . interior is of the occlusal . . ." change to --. . . interior of the occlusal . . .--

Column 9, line 12, ". . . stream of substances,: and in particular . . ." change to --. . . stream of substances, and in particular . . .--

Column 10, line 46, ". . . as described with, regard to the . . ." change to --. . . as described with regard to the . . .--

Column 13, line 17, ". . . at the delivery end 401 a is punctured, . . ." change to --. . . at the delivery end 401$a$ is punctured, . . .--

Column 18, line 66, ". . . Means for selectively and control lably . . ." change to --. . . Means for selectively and controllably . . .--

UNITED STATES PATENT AND TRADEMARK OFFICE
CERTIFICATE OF CORRECTION

PATENT NO.       : 6,656,151 B1
APPLICATION NO.  : 09/480964
DATED            : December 2, 2003
INVENTOR(S)      : Blatter It is certified that error appears in the above-identified patent and that said Letters Patent is hereby corrected as shown below:

Column 24, line 23, ". . . for delivering, fluids into or . . ." change to --. . . for delivering fluids into or . . .--

Signed and Sealed this

Twentieth Day of May, 2008

JON W. DUDAS
*Director of the United States Patent and Trademark Office*